US010463858B2

(12) United States Patent
Perryman et al.

(10) Patent No.: US 10,463,858 B2
(45) Date of Patent: Nov. 5, 2019

(54) DEVICES AND METHODS FOR TREATING CRANIOFACIAL PAIN

(71) Applicant: MICRON DEVICES, LLC, Miamia Beach, FL (US)

(72) Inventors: Laura Tyler Perryman, Miami Beach, FL (US); Chad Andresen, Miami Beach, FL (US)

(73) Assignee: Stimwave Technologies Incorporated, Pompano Beach, FL (US)

( * ) Notice: Subject to any disclaimer, the term of this patent is extended or adjusted under 35 U.S.C. 154(b) by 133 days.

(21) Appl. No.: 14/775,455

(22) PCT Filed: Mar. 14, 2014

(86) PCT No.: PCT/US2014/029681
§ 371 (c)(1),
(2) Date: Sep. 11, 2015

(87) PCT Pub. No.: WO2014/153218
PCT Pub. Date: Sep. 25, 2014

(65) Prior Publication Data
US 2016/0038741 A1    Feb. 11, 2016

Related U.S. Application Data

(63) Continuation-in-part of application No. PCT/US2013/073326, filed on Dec. 5, 2013, and a
(Continued)

(51) Int. Cl.
*A61N 1/00*    (2006.01)
*A61N 1/36*    (2006.01)
(Continued)

(52) U.S. Cl.
CPC ....... *A61N 1/36071* (2013.01); *A61N 1/3756* (2013.01); *A61N 1/37205* (2013.01); *A61N 1/0551* (2013.01); *A61N 1/3787* (2013.01)

(58) Field of Classification Search
CPC ................ A61N 1/0526; A61N 1/0551; A61N 1/36071; A61N 1/37205; A61N 1/3756; A61N 1/3787
See application file for complete search history.

(56) References Cited

U.S. PATENT DOCUMENTS

2003/0018368 A1* 1/2003 Ansarinia ............ A61N 1/3605
607/46
2006/0047325 A1    3/2006 Thimineur et al.
(Continued)

OTHER PUBLICATIONS

Authorized officer Blaine R. Copenheaver, International Search Report and Written Opinion in PCT/US2014/029681, dated Aug. 20, 2014, 11 pages.

*Primary Examiner* — Lindsey G Wehrheim
(74) *Attorney, Agent, or Firm* — Fish & Richardson P.C.

(57) ABSTRACT

Some implementations provide a method for treating craniofacial pain in a patient, the method including: placing a wirelessly powered passive device through an opening into a target site in a head or neck region of the patient's body, the wirelessly powered passive device configured to receive an input signal non-inductively from an external antenna; positioning the wirelessly powered passive device adjacent to or near a nerve at the target site; and causing neural modulation to the nerve through one or more electrodes on the wirelessly powered passive device.

14 Claims, 27 Drawing Sheets

Related U.S. Application Data continuation-in-part of application No. 13/551,050, filed on Jul. 17, 2012, now Pat. No. 9,409,030, and a continuation-in-part of application No. 13/562,221, filed on Jul. 30, 2012, now Pat. No. 9,199,089, and a continuation-in-part of application No. 13/584,618, filed on Aug. 13, 2012, now Pat. No. 8,849,412, and a continuation-in-part of application No. 13/621,530, filed on Sep. 17, 2012, now Pat. No. 9,242,103, and a continuation-in-part of application No. 14/045,764, filed on Oct. 3, 2013, now Pat. No. 9,220,897.

(60) Provisional application No. 61/786,131, filed on Mar. 14, 2013.

(51) Int. Cl.
*A61N 1/372* (2006.01)
*A61N 1/375* (2006.01)
*A61N 1/05* (2006.01)
*A61N 1/378* (2006.01)

(56) References Cited

U.S. PATENT DOCUMENTS

| | | | |
|---|---|---|---|
| 2008/0103558 A1* | 5/2008 | Wenzel | A61N 1/36014 607/61 |
| 2008/0132982 A1* | 6/2008 | Gerber | A61N 1/0558 607/118 |
| 2010/0204568 A1 | 8/2010 | Narouze | |
| 2011/0190849 A1* | 8/2011 | Faltys | A61N 1/36053 607/50 |
| 2012/0283800 A1* | 11/2012 | Perryman | A61N 1/36142 607/60 |
| 2013/0310901 A1* | 11/2013 | Perryman | A61N 1/0558 607/72 |

* cited by examiner

DEVICES AND METHODS FOR TREATING CRANIOFACIAL PAIN

CROSS REFERENCE TO RELATED APPLICATIONS

This application claims benefit of U.S. provisional Patent Application 61/786,098, filed Mar. 14, 2013. Under 35 U.S.C. 365 and 120, this application claims the benefit of and is a continuation in part of PCT application PCT/US2013/073326, filed Dec. 5, 2013, U.S. patent application Ser. No. 13/551,050 filed Jul. 17, 2012, U.S. patent application Ser. No. 14/045,764 filed Oct. 3, 2013, U.S. patent application Ser. No. 13/562,221, filed Jul. 30, 2012, U.S. patent application Ser. No. 13/584,618, filed Aug. 13, 2012 and U.S. patent application Ser. No. 13/621,530, filed Sep. 17, 2012. The disclosures of these applications are incorporated by reference in their entirety for all purposes.

TECHNICAL FIELD

This application relates generally to the modulation of neural tissue through electrical stimulation.

BACKGROUND

Modulation of neural tissue in the body by electrical stimulation has become an important type of therapy for patients with chronic disabling conditions, including chronic pain, problems of movement initiation and control, involuntary movements, vascular insufficiency, heart arrhythmias, craniofacial pain and more. A variety of therapeutic intra-body electrical stimulation techniques can be used to treat these conditions. Typically, such devices utilize a subcutaneous battery operated implantable pulse generator (IPG) to provide power or other charge storage mechanisms.

SUMMARY

In one aspect, some implementations provide method for treating craniofacial pain in a patient, the method including: placing a wirelessly powered passive device through an opening into a target site in a head or neck region of the patient's body, the wirelessly powered passive device configured to receive an input signal non-inductively from an external antenna; positioning the wirelessly powered passive device adjacent to or near a nerve at the target site; and causing neural modulation to the nerve through one or more electrodes on the wirelessly powered passive device.

Implementations may include one or more of the following features. Placing the wirelessly powered passive device may include advancing the wirelessly powered passive device through an inner lumen of an introducer with a size of 14 gauge or smaller. Placing the wirelessly powered passive device may include placing the wirelessly powered passive device through a surgical incision made on the patient's body. Placing the wirelessly powered passive device may include placing the wirelessly powered passive device percutaneously into the patient's body. Placing the wirelessly powered passive device may include placing the wirelessly powered passive device subcutaneously into the patient's body.

Positioning the wirelessly powered passive device may include advancing a wirelessly powered passive device paddle to reach the nerve at the target site. Positioning the wirelessly powered passive device may include advancing a wirelessly powered passive device that is no larger than 0.8 mm in diameter to reach the nerve at the target site.

Causing neural modulation may include causing neural modulation to a occipital nerve or branches thereof. Causing neural modulation may include causing neural modulation to a trochlear nerve or branches thereof. Causing neural modulation may include: causing neural modulation to a nerve of the patient, the nerve including one of: an occipital nerve, a vagus nerve, a trigeminal nerve, a glossopharyngeal nerve, a mandibular nerve, an alveolar nerve, a lingual nerve, a maxillary nerve, a ciliary nerve, a sphenopalatine ganglion, or a supratrochlear nerve.

The method may further include using X-Ray fluoroscopy to guide positioning of the wirelessly powered passive device adjacent to or near the nerve at the target site. The method may further include using ultrasound sonography to guide positioning of the wirelessly powered passive device adjacent to or near the nerve at the target site. The method may further include withdrawing the introducer device from the patient's body after the neural modulation has been confirmed to be effective.

Causing the neural modulation may include causing the input signal to be transmitted from the external antenna outside the patient's body, the input signal including electrical power and excitation pulses to drive the one or more electrodes of the wirelessly powered passive device; causing the input signal to be received non-inductively by one or more antennas on the wirelessly powered passive device; causing the electrical power and excitation pulses to be extracted from the input signal; and based on the electrical power, causing the excitation pulses to be delivered to the one or more electrodes on the wirelessly powered passive device.

Placing a wirelessly powered passive device may further include placing a wirelessly powered passive device that includes (i) one or more non-inductive antennas configured to receive electromagnetic energy radiated from a source located outside of the patient's body, (ii) electronic circuitry coupled to each of the one or more non-inductive antennas and configured to extract electric power and excitation pulses from the radiated electromagnetic energy as received by the one or more non-inductive antennas, and (iii) one or more electrodes configured to deliver the excitation pulses to the one or more excitable tissue to effectuate neural modulation thereof.

In another aspect, a system for treating craniofacial pain includes one or more implantable wirelessly powered passive devices configured to apply one or more electrical pulses to neural tissue of the head and neck, particularly nerves associated with pain or nerve based disorders in the neck, face or cranium. The electrical pulses may be sufficient to modulate the nerves to treat pain and/or neuromuscular disorders. The devices are radiatively coupled to an external pulse generating transmitter for generating the electrical pulses.

The pulse generating transmitter is not physically attached to the implantable wirelessly powered passive device. The wirelessly powered passive device of a treatment system may include a first antenna coupled for receiving an input signal from a second antenna, remote from the first antenna. The second antenna may be external to the patient's body or it may be positioned on the patient's body or implanted within the patient's body remotely from the first antenna on the wirelessly powered passive device. The second antenna may be located on an external pulse generating transmitter, different and separate from the wirelessly powered passive device. In some implementations, the second antenna is configured to transmit the input signal, which includes the electrical pulses and electrical power, to the first antenna on the implanted wirelessly powered passive device. The first antenna is configured to receive the input signal. Electronic circuitry may be coupled to the first antenna and located on the wirelessly powered passive device. The electronic circuitry may be configured to extract the electrical pulses from the received input signal. The electronic circuitry may provide the electrical pulses to one or more electrodes of the wirelessly powered passive device. In this manner, the electrical pulses may be applied one or more excitable tissue adjacent to or near the one or more electrodes. In one configuration, the one or more electrodes and the antenna are housed within an enclosure of the wirelessly powered passive device. The enclosure may be configured for subcutaneous placement on the patient's body or percutaneous placement into deeper tissue structures within the patient's body. The placement of the wirelessly powered passive device may be accomplished by the use of an introducer. The placement of the wirelessly powered passive device may be guided by fluoroscopy, including X-Ray and ultrasound, to verify that the introducer is in the correct position.

In another aspect, a method for stimulating one or more of the occipital, vagus, trigeminal, glossopharyngeal, mandibular, alveolar, lingual, maxillary, ciliary, sphenopalatine ganglion, and the supratrochlear nerves is disclosed. In one example method, one or more wirelessly powered passive devices are advanced percutaneously and/or subcutaneously to a target site on or adjacent to the nerve such that an electrical pulse may be applied to the electrodes of the wirelessly powered passive device to modulate the nerves at the target site. In one configuration, an input signal containing electrical energy is delivered to a first antenna within the wirelessly powered passive device. The input signal may be converted to electrical pulses, which may then be applied to the electrodes of the wirelessly powered passive device for modulating the nerves at the target site. In one aspect, the input signal is transmitted from a second antenna physically separate from the first antenna and positioned either external to the patient's body or in a location on or in the patient's body separate from the first antenna of the wirelessly powered passive device. In certain embodiments, the wirelessly powered passive devices are surgically implanted at the target site. In other embodiments, the wirelessly powered passive device may be percutaneously advanced to the target site and the introducer is withdrawn upon conclusion of the placement.

In another aspect, a method for stimulating nasopalatine nerves may include positioning (e.g., implanting) one or more wirelessly powered passive devices in or near the nasal cavity of the patient and applying an electrical pulse to the electrodes sufficient to modulate one or more of the nasopalatine ganglion, the anterior palatine, the middle palatine, the posterior palatine, the facial nerve, nasal branches, ethimoidal nerves or the sphenopalatine ganglion.

The methods described above may include providing a wirelessly powered passive device including an enclosure that houses: one or more electrodes; a first antenna configured to receive, from a second antenna and through electrical radiative coupling, an input signal containing electrical energy, the second antenna being physically separate from the implantable lead; one or more flexible circuits electrically connected to the first antenna, the flexible circuits configured to: create the one or more electrical pulses suitable to be applied at the electrodes using the electrical energy contained in the input signal; and supply the one or more electrical pulses to the one or more electrodes, and implanting the wirelessly powered passive device into a patient's body through an introducer, such as a needle.

In another aspect, a system for stimulating neural tissue comprises a controller module having a first antenna external to the patient's body and configured to send an input signal containing electrical energy to a second antenna through electrical radiative coupling. The second antenna is a dipole antenna and is located in an enclosure in the wirelessly powered passive device, such as those described above. The wirelessly powered passive device does not include an internal power source. The circuits of the wirelessly powered passive device may include only passive components. The input signal has a carrier frequency in the range of about 300 MHz to about 8 GHz, preferably between about 750 MHz to about 2.5 GHz.

In another aspect, an implantable wirelessly powered passive device includes an enclosure shaped and configured for percutaneous delivery into a patient's body through an introducer, such as a needle, to a target site at a cranial or facial nerve. The enclosure houses one or more electrodes configured to apply one or more electrical pulses to a neural tissue. The enclosure preferably also houses a first antenna configured to receive, from a second antenna through electrical radiative coupling, an input signal containing electrical energy. The second antenna may be physically separate from the implantable wirelessly powered passive device and may be positioned external to the patient's body. In some cases, the first antenna is a dipole antenna. The enclosure further comprises one or more circuits electrically connected to the first antenna and configured to create the one or more electrical pulses suitable for stimulation of the neural tissue using the electrical energy contained in the input signal and to supply the one or more electrical pulses to the one or more electrodes.

A portion of the enclosure may leave the electrodes in a non-direct contact with the neural tissue after the wirelessly powered passive device has been delivered into the subject's body. The enclosure can be semi-cylindrical or flat in shape and the electrodes may include at least one directional electrode that directs a current path associated with the one or more electrical pulses to a direction that is substantially perpendicular to the neural tissue. The wirelessly powered passive device may include a semi-cylindrical or flat array of electrodes. The electrodes may be made of at least one of platinum, platinum-iridium, gallium-nitride, titanium-nitride, iridium-oxide, or combinations thereof. The electrodes may include two to sixteen electrodes, each having a longitudinal length between about 0.25 and 6.0 mm and a diameter between about 0.1 and 0.8 mm. The electrodes are spaced between about 0.25 mm to 6 mm apart and have a combined surface area of between about 0.19 $mm^2$ to 250.0 $mm^2$.

The enclosure may include a feature allowing for mating of a stylet that does not extend the length of the wirelessly powered passive device. The stylet-mating feature can be concave on the proximal portion of the wirelessly powered passive device with a length of between about 0.1 mm and 1.0 mm. The stylet-mating feature may be semi-spherical or may be an asymmetrical shape for further steerability of the wirelessly powered passive device. The enclosure may further include a distal tip. The distal tip can be rounded with a length of between about 0.1 mm and 2.0 mm. The distal tip can also be pointed with a length of between about 0.1 mm and 6.0 mm. The enclosure may have an external coating of biocompatible polymer, the polymer includes at least one of polymethymethacrylate (PMMA), polydimethylsiloxane (PDMS), parylene, polyurethance, polytetrafluoroethylene (PTFE), or polycarbonate. The enclosure may further have an external coating of silicone elastomer. The enclosure can further house antenna coupling contacts, the antenna contacts being electrically connected to the antennas and the circuit and configured to couple the antenna with the surrounding tissue. The antenna coupling contacts can include two to eight antenna-coupling pairs. The antenna coupling contacts may be located proximal, relative to the electrodes, in the enclosure. The antenna coupling contacts can each have a longitudinal length of between about 0.1 mm and 6.0 mm, and a diameter of between about 0.1 mm to 0.8 mm. The antenna coupling contacts can be spaced between about 10 mm and 80 mm apart. At least one of the antennas can be constructed as a conductive trace contained on one of the circuits. At least one of the antennas can be fabricated as a conductive wire connected to one of the circuits. The circuits can be flexible circuits. The flexible circuits are capable of undergoing a bend radius of under 0.5 mm. The flexible circuits can be placed proximal, relative to the electrodes, in the enclosure. The flexible circuits can include a waveform conditioning circuit.

In yet another aspect, a stylet is configured to aid in the surgical placement of the wirelessly powered passive device. The stylet fits through the inner diameter of a tuohy needle no greater than 14 gauge, and may contain a feature for mating the stylet to an implantable wirelessly powered passive device. On the distal tip of the stylet is a mating feature, which may be semi-spherical, and grips the implantable wirelessly powered passive device during placement. Other features may include alternative extruded shapes for mating the stylet to the wirelessly powered passive device. The mating feature may only extrude from the distal tip of the stylet from between about 0.1 mm and 1.0 mm and does not fill the body of the wirelessly powered passive device. The mate between the wirelessly powered passive device and the stylet is active only during distal directional movement of the stylet. The stylet may have a longitudinal length of between about 50 mm and 177 mm. The stylet may have a diameter in the range from between about 0.1 mm and 0.9 mm. The stylet may be made of a rigid biocompatible material such as stainless steel, titanium, nylon, or polyethylene. The mating feature may have a surface material that allows for increased friction such as silicon or polyurethane to improve the mate between the stylet and the implantable wirelessly powered passive device.

Some embodiments of the stylet include a central lumen that contains a plunger used for creating a negative pressure port on the distal tip. The negative pressure port exits where the mating feature connects to the wirelessly powered passive device. This suction stylet can grip the implantable wirelessly powered passive device during distal and proximal directional movement. The suction stylet may have a locking feature that allows for the plunger pressure level to be maintained without the operator maintaining the force on the plunger.

In another aspect, a method for treating occipital nerves comprises positioning one or more electrodes at a target site adjacent or on one or more nerves in the head or neck of a patient and applying an electrical impulse to the electrodes sufficient to modulate the occipital nerve. The wirelessly powered passive device may be in the shape of a paddle which is surgically placed subcutaneously along the occipital crest targeting the occipital nerve bundles. The paddle wirelessly powered passive device may include, for example, four electrodes and the spacers between the electrodes. The paddle wirelessly powered passive device can include between two to sixteen electrodes located on the distal end.

In yet another aspect, methods and devices are disclosed for stimulating trochlear nerve bundles. In a method, one or more electrodes are advanced through injection or small incisions to a target site adjacent or on a trochlear nerve and an electrical impulse is applied to the electrodes to modulate the trochlear nerve. In certain embodiments, the electrodes comprise implantable leads such as those described above that are cylindrical or semi-cylindrical. In other embodiments, the electrodes comprise wireless paddle leads.

DETAILED DESCRIPTION OF THE INVENTION

Figure 1:
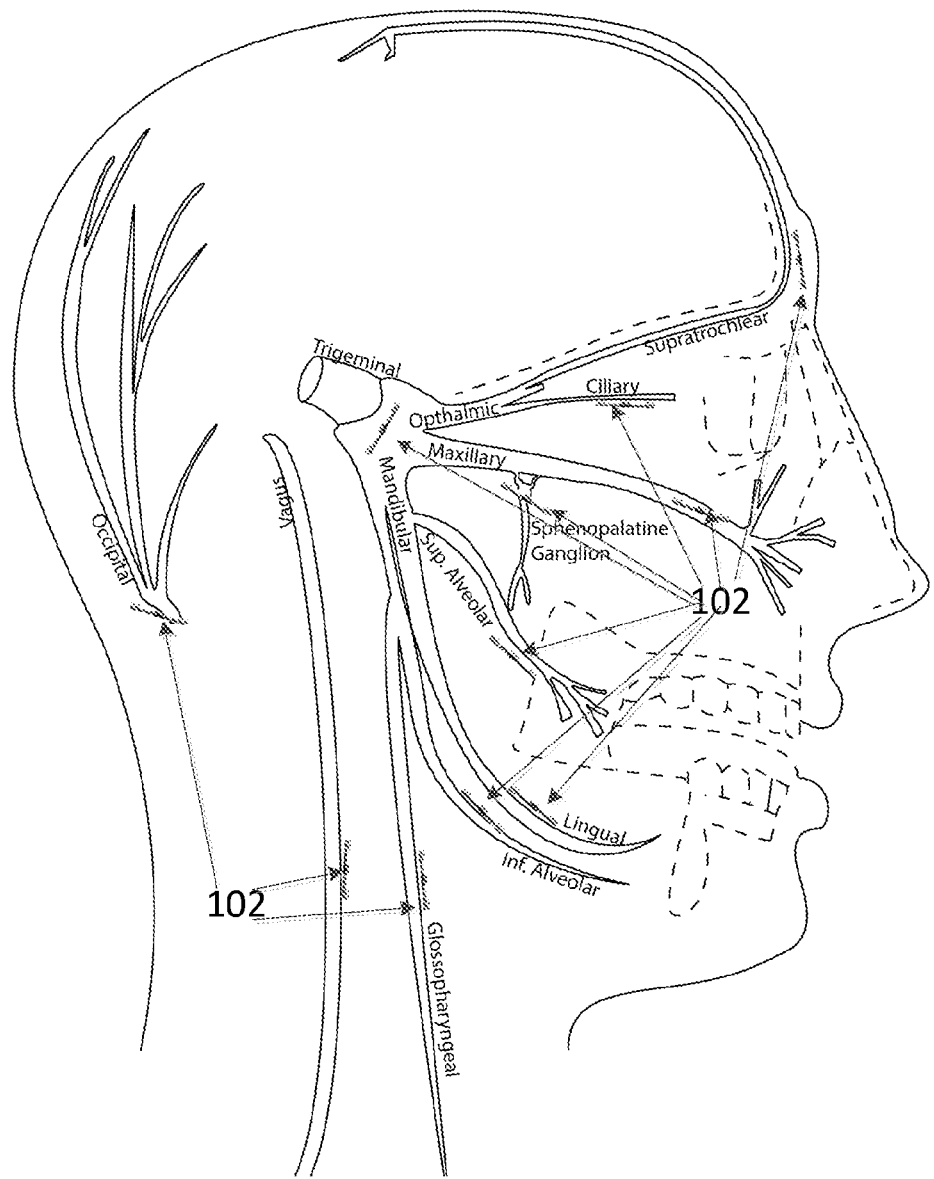
FIG. 1 illustrates the anatomical wirelessly powered passive device placements for targeting the sphenopalatine ganglion, alveolar nerve, vagus nerve, lingual nerve, laryngeal nerve, mandibular ganglion, trigeminal nerve, maxillary nerve, occipital nerve bundle, supratrochlear nerve, and facial nerve.

Facial pain generally occurs after sinus or dental surgery, or skull or facial trauma. The etiology of pain depends on the precipitating event. Acute rhinosinusitis often presents with pain located over the affected sinus. Cranial facial pain can be caused by several underlying disorders. Trigeminal neuralgia is a nerve disorder that causes a stabbing or electric-shock-like pain in parts of the face. Temporormandibular joint (TMJ) syndrome is a malfunction of the TMJ that controls the jaw, leading to facial pain. Other causes could be attributed to Persistent idiopathic facial pain (PIFP), PIFP refers to pain along the trigeminal nerve that does not fit the classic presentation of other cranial neuralgias. The duration of the pain is usually long, lasting most of the day, and may be continuous. The pain is unilateral and may be described as a severe ache, crushing sensation, or burning sensation.

In various implementations, a neural stimulation system and method is disclosed for applying one or more electrical pulses to targeted facial or cranial nerve tissue to treat craniofacial pain, such as trigeminal neuralgia, trigeminal neuropathic or deafferentation pain, temporomandibular joint (TMJ) syndrome, persistent idiopathic facial pain (FIFP), post-herpetic neuralgia, chronic daily headache, trigeminal neuropathic pain, post-stroke pain, thalamic pain, bulbar pain, nociceptive pain, cluster headache, migraine headaches, atypical facial pain, occipital neuralgia, occipital headache, craniofacial pain of neuropathic origin and the like. Neuropathic origin generally refers to pain as a result of direct or indirect neural injury from trauma, surgery, infection, neoplasm, congenital defect or metabolic disease. The targeted nerve tissues may be, for example, in the nasopalatine ganglion, the anterior palatine, the middle palatine, the posterior palatine, the facial nerve, supraorbital and infraorbital nerves, trigeminal nerves, nasal branches, or the ethimoidal. Additional nerves, such as the occipital, motor cortex, vagus, glossopharyngeal, mandibular, alveolar, lingual, maxillary, ciliary, sphenopalatine ganglion, and the supratrochlear may also be treated.

The neural stimulation system can include a wirelessly powered passive device that includes an enclosure that houses one or more conductive antennas (for example, dipole or patch antennas), internal circuitry for electrical pulse and electrical energy rectification, and one or more electrode pads allowing for neural stimulation of tissue. The neural stimulation system may further comprise an external controller and antenna for sending radio frequency or microwave energy from an external source to the implantable wirelessly powered passive device with neither cables nor inductive coupling for power.

The implantable wirelessly powered passive device is passive, that is, with no on board power source. The wireless passive device may also be known as an implantable lead. The wirelessly powered passive device may be implanted in the first facial plane (FFP) of the patient where the electrodes are exposed to facilitate electrical stimulation. The external transmitting antenna may be house on an external pulse generator, worn outside of the patient's body. The external pulse generator may be wirelessly coupled with the implanted wirelessly powered passive device. The external pulse generator may be programmed by the clinician to send the desired stimulation parameters through the transmitting antenna and wirelessly transfer it to the implanted wirelessly powered passive device. The implantable wirelessly powered passive devices may be passive and not protrude out of the skin. In certain situations, they may not produce any effect except when powered by energy from the transmitter. Stimulation programs and batteries may be maintained outside of the patient's body for ease of access, thereby mitigating the risks associated with traditional implantable pulse generator systems.

The external components may be accessible by the patient or clinician and may transcutaneously transfer stimulation parameters or programs to the implanted wirelessly powered passive device. To judiciously place the implanted wirelessly powered passive device for stimulation, a trained physician may access the subcutaneous tissue and perform the implantation procedure. The implant procedure may be minimally invasive, allowing for percutaneous implantation using a needle as the carrier vehicle. The patient may arrive at the clinic for a one-day procedure (or out-patient procedure) where the physician will insert and drive the needle to the implant location. The implantable wirelessly powered passive device may be pushed through the inner lumen of the needle to the final resting location. The needle may then be removed, and if necessary a second implantable wirelessly powered passive device can be implanted adjacent to the first. The "tail" end of the lead may be position to rest just below the skin so that the wirelessly powered passive device can be easily located and accessed when the device needs to be removed. Once implanted, test stimulation can begin by placing the external antenna over the wirelessly powered passive device to power the device. The RF signals may emanate from the external antenna to arrive on the receiving antenna(s) of the implanted wirelessly powered passive device through non-inductively coupling. This RF signal may be processed and translated into an electrical current used for stimulation of the patient's nerve.

In various embodiments, the implantable wirelessly powered passive device is powered wirelessly (and therefore does not require a wired connection) and contains the circuitry necessary to receive the pulse instructions from a source external to the body. Some example implementations are discussed in association with FIGS. 6-16.

Various embodiments may include distinct advantages over wired devices in regards to ease of insertion, cross connections, elimination of extension wires, and no requirement for an implantable pulse generator in order to administer a chronic therapy. Various implementations also may have an associated lower overall cost compared to existing implantable neural modulation systems due to the elimination of the implantable pulse generator and this may offer wider adoption of neural modulation therapy for patients as well as reduction in overall cost to the healthcare system.

Referring to FIG. 1, in some implementations, facial nerves are modulated with the system and devices described herein. The nerves that can be treated by a wirelessly powered passive device include, but are not limited to, the occipital, vagus, trigeminal, glossopharyngeal, mandibular, alveolar, lingual, maxillary, ciliary, sphenopalatine ganglion, and the supratrochlear. As illustrated, implantable wirelessly powered passive devices 102 may be implanted at various target locations within the facial cranial cavity to modulate an excitable tissue, for example, a nerve. Various wirelessly powered passive devices that may be used are described below. The depths of these nerves may range between about 2.0 mm and 1.0 cm, but are accessible and treatable through minimally invasive operations and injections. An example wirelessly powered passive devices can contain between 1 and 8 electrodes, with a diameter from between 0.1 mm to 1.4 mm. The electrodes each may have a longitudinal length of between about 0.25 mm and about 6.0 mm from the distal tip toward the proximal tip. The spacing between the electrode contacts may be between about 0.25 mm and about 6.0 mm. The total electrode surface area of the wirelessly powered passive device body may be between about 0.19 mm$^2$ and about 250.0 mm$^2$. A patient may have, for example, up to eight wirelessly powered passive devices implanted while still being able to receive electrical power and electrical pulses wirelessly for each implanted wirelessly powered passive device to stimulate excitable tissue at the target site can be stimulated.

The following describes an example of a procedure for implanting a wirelessly powered passive device 102. An incision site may be placed on the facial cranial region of a subject patient. The subject may be placed in a supine position. The incision site can be prepared using standard surgical precautions and sterilization techniques. For example, prophylactic antibiotics may be administered according to the standard protocol of the institution providing the implantation service. Local anesthetic may be administered to anesthetize the skin and subcutaneous tissues at the intended site of entry. Using fluoroscopy (for example, X-Ray or ultrasound), the implant site location may be targeted and the desired entry level for device placement can be marked.

Implantable wirelessly powered passive device 102 may be introduced into the subcutaneous tissue area between the dermis and the 1$^{st}$ fascial layer (FFL). Under fluoroscopy (for example, X-Ray or ultrasound), a physician may insert the needle near the respective craniofacial nerve. The physician may slowly insert the wirelessly powered passive device through an inner lumen of the needle, rotating the device tip to steer the device 102 toward the target site. The insertion process of the device 102 may be aided by a stylet, such as the ones described below. The clinician may then confirm the device placement using Anterior-Posterior (A-P) and Lateral fluoroscopy. Then, the clinician may detach the stylet from the device 102 while leaving device 102 in the target position. Thereafter, the clinician may remove the stylet from the implanted device. The clinician may test a stimulation protocol on the patient and the patient may be instructed to verbally express whether the treatment causes pain or discomfort. If the patient expresses discomfort, the clinician may adjust the amplitude of excitation pulses immediately. In some instances, the excitation pulse amplitude may be lowered to reduce discomfort to the patient. During a treatment protocol, the clinician may set a low stimulation setting in order to acquire feedback from the patient regarding where the stimulation is felt. Once a majority of the primary pain area is covered with the stimulation feeling, as reported by the patient, the treatment protocol may proceed to the next treatment session (or target area).

In some configurations, the stimulation parameters may be set initially to include, for example, 200 μs pulse width, 0 mA amplitude, and 50 Hz frequency. To match the stimulation sensation pattern (paresthesia) against pain pattern distribution, the stimulation parameters may be slowly adjusted based on patient feedback regarding perception thresholds, as discussed above. For instance, the stimulator parameters may be adjusted upward until paresthesia is felt in the primary pain area. If, however, paresthesia is being felt in other areas of the body, the physician may reposition the device 102 until the paresthesia location and the primary pain site overlap. Then, the position of the device 102 may be recorded. Thereafter, stimulation can be applied through device 102 until the anticipated suppression of pain is achieved (for example, at least 75% coverage of primary pain area). In some configurations, pain relief may require 50-100 Hz of pulse repetition rate for more than 30 minutes. If paresthesia is not achieved within the range of the parameters (for example, repetition rate of under 100 Hz and duration of therapy under 40 minutes), the following settings may be adjusted one at a time until paresthesia covers, for example, at least 75% of the primary pain area. In one example, the pulse amplitude may be adjusted higher in increments of, for instance, 0.5 mA to a max of about 10 mA. In another example, the pulse width may be adjusted higher, for example, in increments of 50 μs up to a max of about 450 μs. In some configurations, if paresthesia is not achieved, the repetition rate (or frequency) of the excitation pulses may be adjusted higher, for instance, in increments of 10 Hz up to max of about 120 Hz. Changing the frequency of excitation pulses may not change paresthesia location, but may alter paresthesia intensity. Generally speaking, if paresthesia is not achieved after various parameter combinations have been attempted, implantable device 102 may be repositioned.

The clinician may record the final location of device 102 that best aligns the paresthesia and the primary pain area. The physician may record the final frequency and pulse width used to achieve, for example, 50% pain relief. If paresthesia is not achieved, a second device may be implanted at the physician's discretion. If paresthesia coverage has reached, for example, in a majority of the primary pain area, then the proximal end of device 102 may be anchored using sutures or sterile tape.

Figure 2:
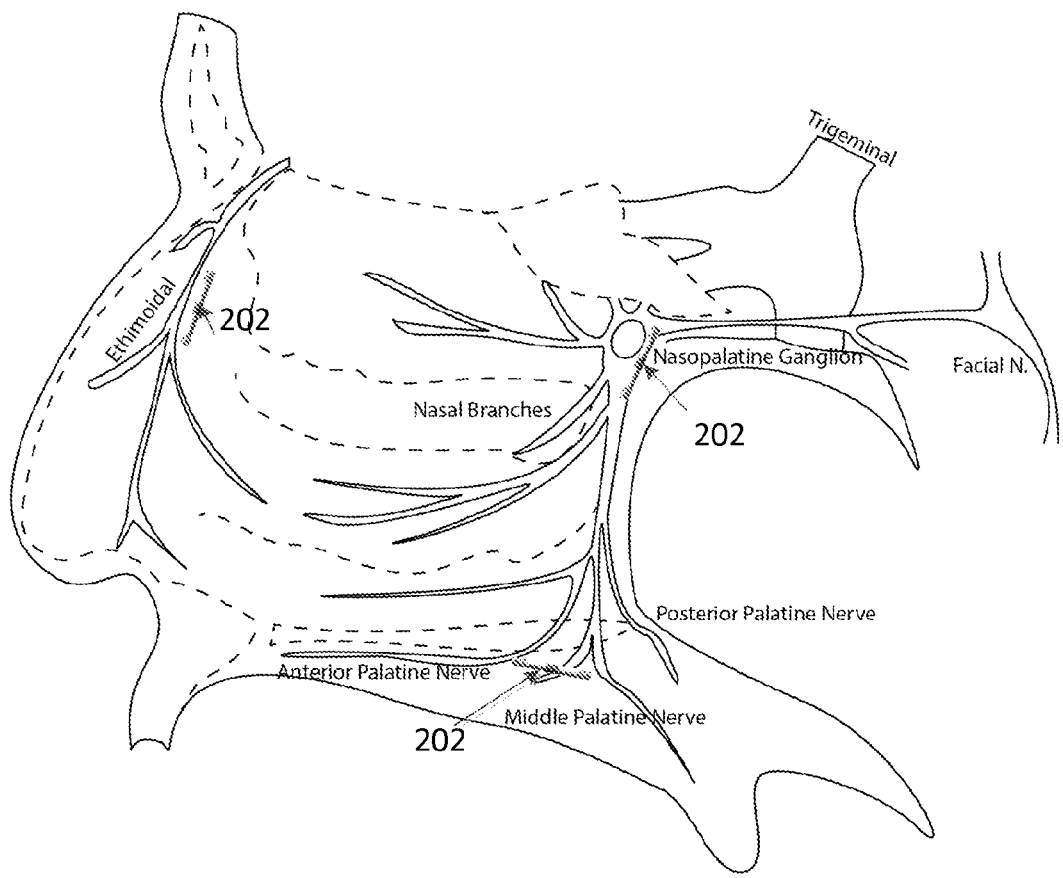
FIG. 2 illustrates the anatomical wirelessly powered passive device placements for targeting the nasopalatine nerve targets.

FIG. 2 illustrates placements of wirelessly powered passive devices 202 to modulate nasal nerves. For modulating nerves in the nasal region, wirelessly powered passive devices 202 may be implanted using a more invasive implantation approach. Nasopalatine stimulators may require a more invasive surgery than the subcutaneous placements described above in reference to FIG. 1. The nerves targeted under the nasopalatine approach may include but are not limited to the nasopalatine ganglion, the anterior palatine, the middle palatine, the posterior palatine, the facial nerve, nasal branches, or ethimoidal. In some instances, a wirelessly powered passive device as described above and in FIGS. 6-19 can be used for nasopalatine nerve modulation. In other instances, a paddle wirelessly powered passive device as described in FIGS. 5A and 5B may be used for nasopalatine nerve modulation. The placement of the wirelessly powered passive device, for example, a paddle form factor, may be performed by using an introducer, in addition to surgical placements. For illustration, the wirelessly powered passive device may be inserted through an inner lumen of the introducer into a patient. The placement of the wirelessly powered passive device may be guided by fluoroscopy, including X-Ray and ultrasound, to verify that the device has been placed in the correct position.

Figure 3A:
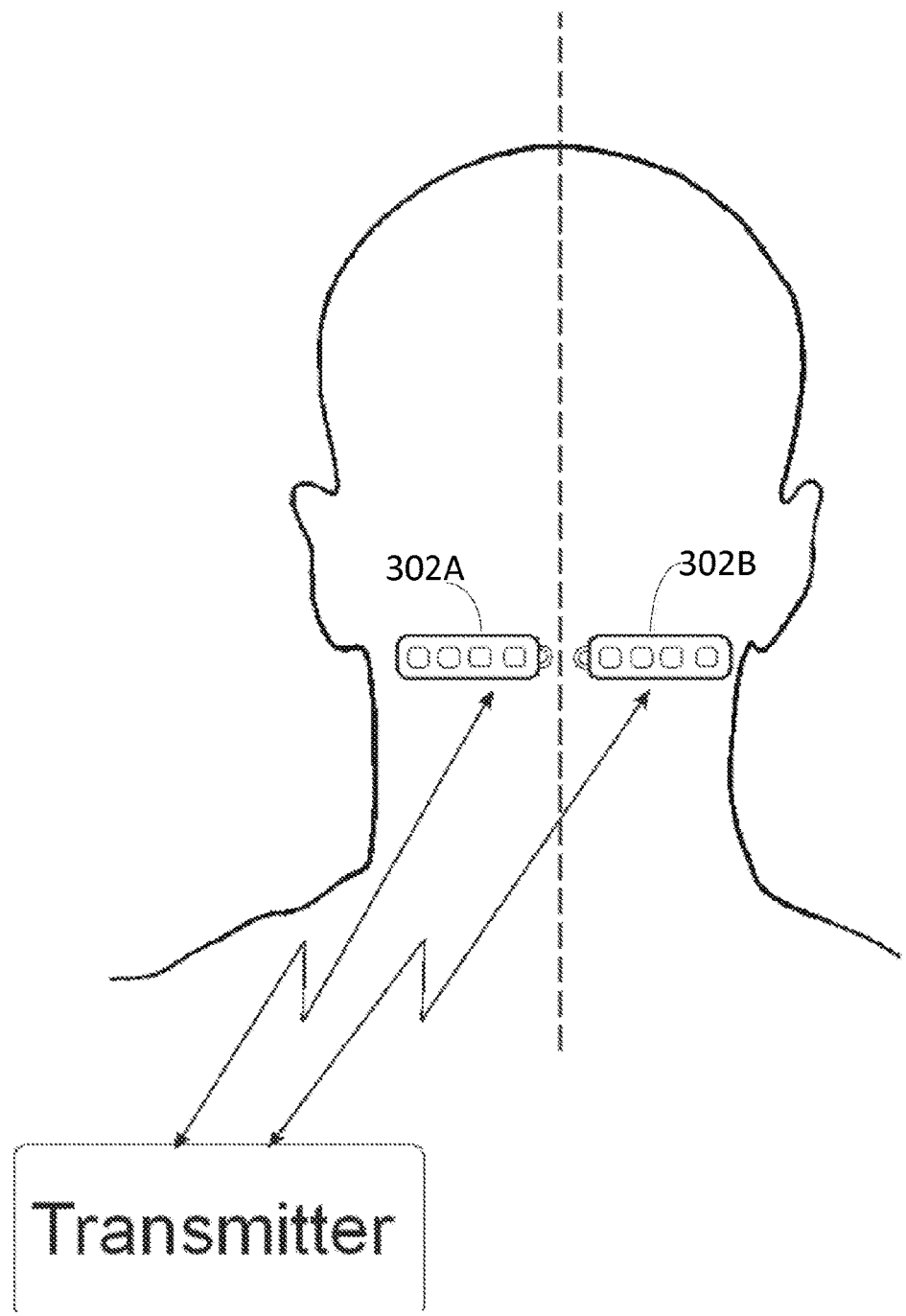
FIG. 3A illustrates an example of a wirelessly powered passive device paddle form factor placed for targeting the occipital nerve bundle.

Referring now to FIG. 3, a system and method for stimulating occipital nerves is described. As shown, two wirelessly powered passive device paddle form factors 302A and 302B are surgically placed subcutaneously along the occipital crest targeting the occipital nerve bundles. The devices 302A and 302B are placed lateral from the centerline. The devices 302A and 302B may include a small suture feature for anchoring the respective device to surrounding tissue. The wirelessly powered passive device paddle 302A and 302B may include one or more electrodes to apply electrical pulses to nerves in the occipital bundle. As described herein, the wirelessly powered passive device may receive an input signal non-inductively and without a wired connection from an external antenna physically separate (e.g., external to the patient). The input signal may include electrical energy and information regarding electrical pulses to be applied to nerves in the occipital bundle.

Figure 3B:
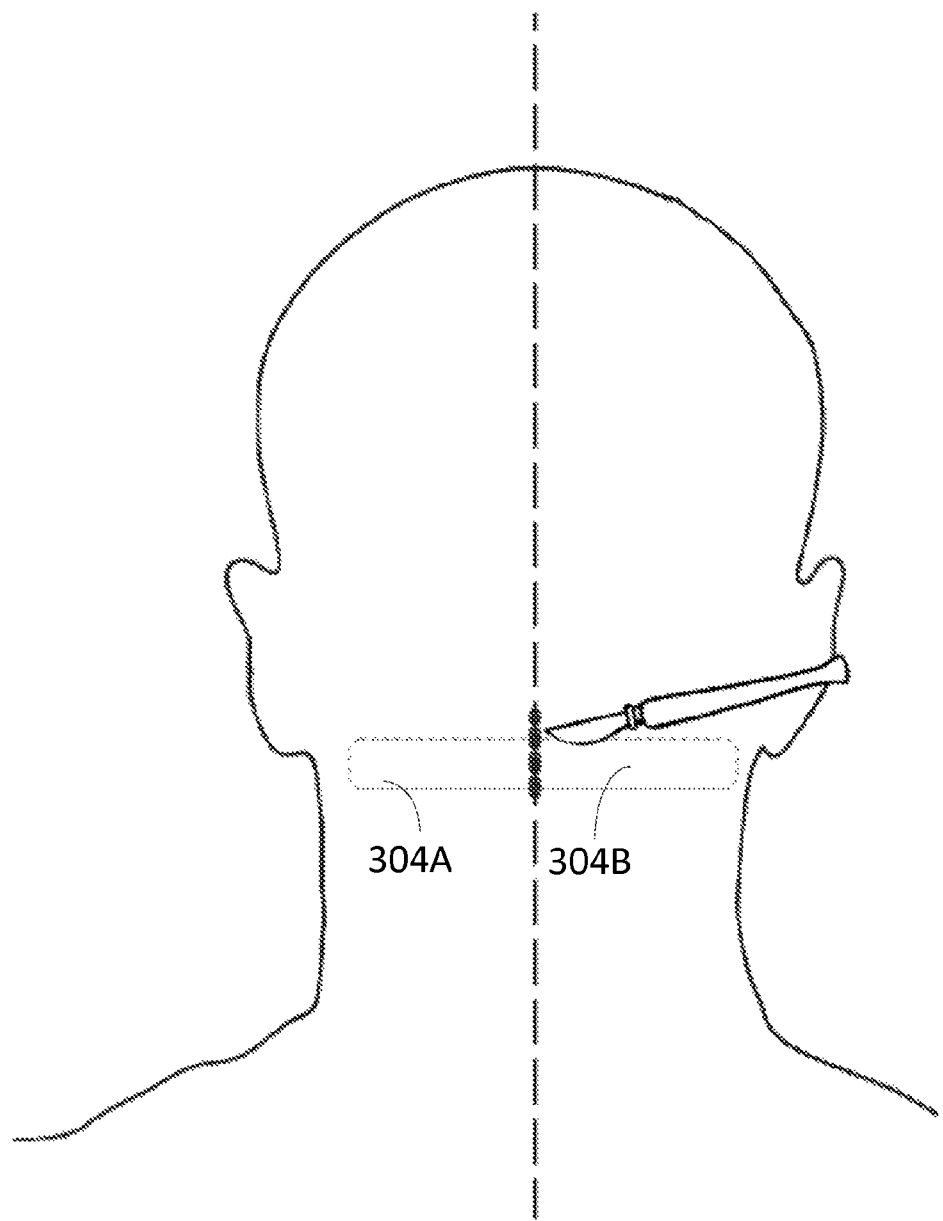
FIG. 3B illustrates an example of a surgical procedure for placing a wirelessly powered passive device paddle form factor for targeting the occipital nerve bundle.

FIG. 3B illustrates the surgical procedure for implanting the wirelessly powered passive device paddle 302A and 302B for targeting the occipital nerve bundle. An incision of between 1 mm and 15 mm may travel caudally along the centerline of the dorsal aspect of the neck. The incision includes a left side 304A (for implanting the wirelessly powered passive device paddle 302A) and a right side 304B (for implanting the wirelessly powered passive device paddle 302B). A small stylet or semi-rigid introducer may be used to make a potential space for the wirelessly powered passive device paddle 302A and 302B. In some implementations, a miniature wirelessly powered passive device such as described in FIGS. 6-19 may be used in place of a paddle-type device. The potential space created by the incision may have a width of between 1 mm and 15 mm. The potential space may have a length of between 1 cm and 5 cm. The height of the potential space may fit a wirelessly powered passive device ranging from between 0.1 mm and 3 mm in diameter or thickness. In one instance, a clinician may inject an introducer device into the patient's body at the incision site. The treating clinician may then place the wirelessly powered passive device through the inner lumen of the introducer into the patient's body towards the target site. The placement procedure may be guided by, for example, X-Ray fluoroscopy or ultrasound sonography. Once the wirelessly powered passive device has reached the target site, the clinician may anchor the wirelessly powered passive device to a surrounding tissue by, for example, suturing the wirelessly powered passive device to the surrounding tissue.

Figure 4:
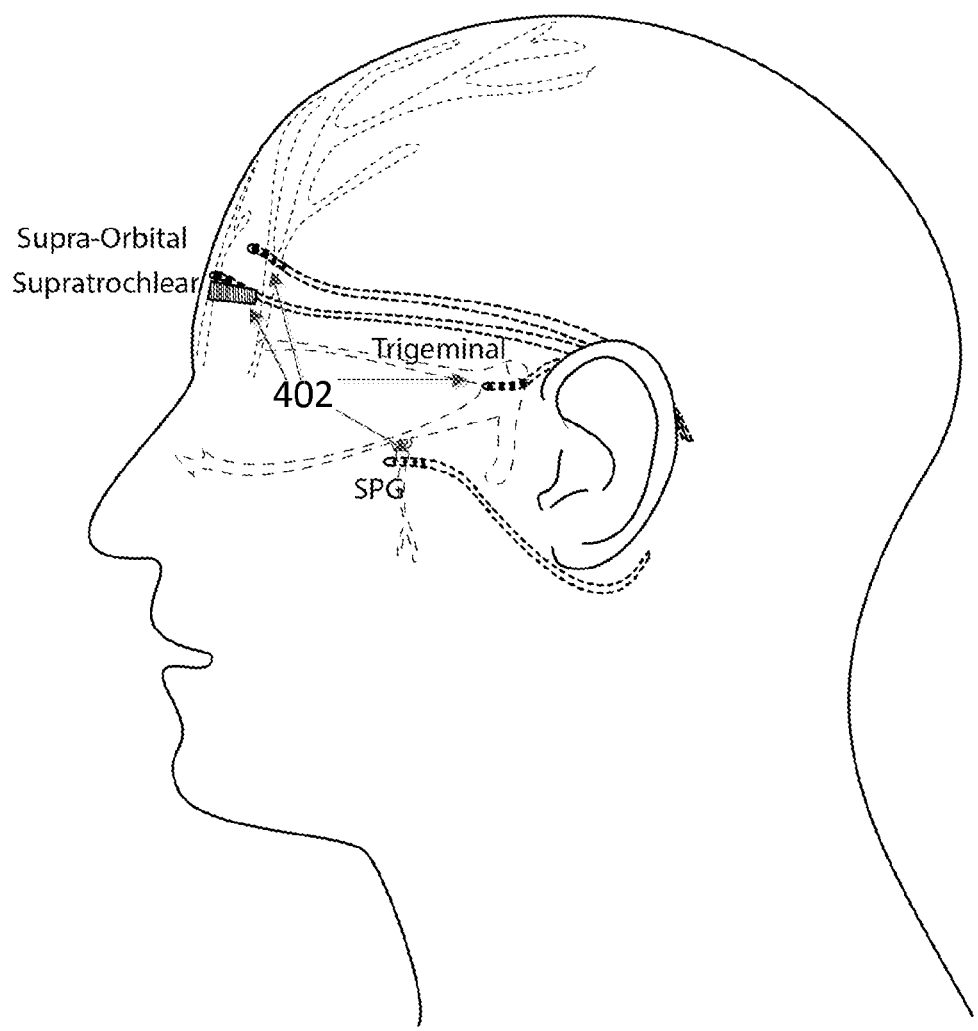
FIG. 4 illustrates an example of subcutaneous wirelessly powered passive device placement for targeting the supratrochlear nerve, supraorbital, trigeminal, and sphenopalatine ganglion.

Referring now to FIG. 4, the trochlear nerves can be stimulated using wirelessly powered passive devices 402. In some instances, implantable wirelessly powered passive devices 402, such as those described in FIGS. 6-16 can be positioned subcutaneously adjacent to or near the trochlear nerves. The wirelessly powered passive devices 402 may be placed through injection or small incisions at a target site according to a variety of implantation methods. In some implementations the wirelessly powered passive devices may include a paddle form factor, such as those described in FIGS. 3A, 3B, 5A and 5B. The wirelessly powered passive device paddle may be placed superior to the ocular brow in a range of between 1.0 mm and 10.0 mm. The wirelessly powered passive device paddle also may be placed targeting the centerline of the forehead and extend laterally towards the ears following the brow line.

Figure 5A:
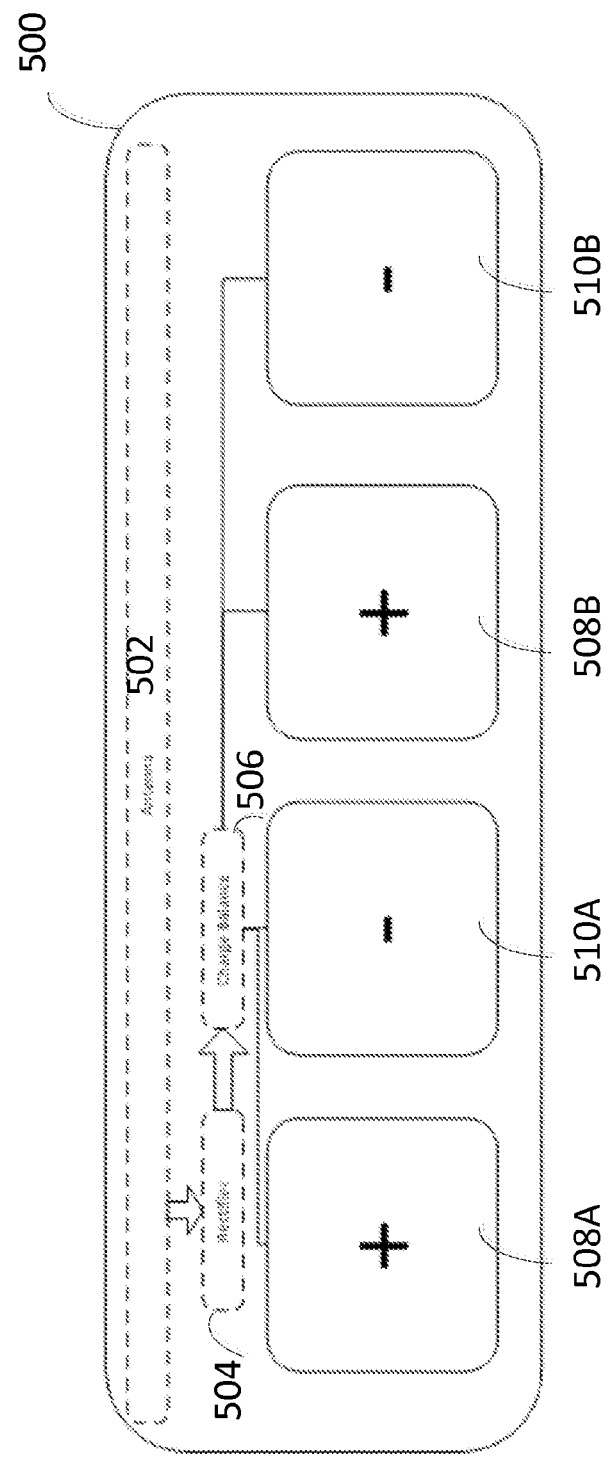
FIG. 5A illustrates an example of a wirelessly powered passive device paddle form factor.

FIG. 5A illustrates an example of a subcutaneous wirelessly powered passive device paddle 500. Wirelessly powered passive device paddle 500 may include, for example, four electrodes 508A, 510A, 508B, and 510B. In some instances, the wirelessly powered passive device paddle 500 can include between two and sixteen electrodes located on the distal end 512 of the device. The electrodes 508A, 510A, 508B, and 510B each may have a longitudinal length between about 1.0 mm and about 6.0 mm from the distal end 512 toward the proximal end 514. The electrodes 508A, 510A, 508B, and 510B each may have a width of between about 0.4 mm and about 3.0 mm. The total electrode surface area of an example wirelessly powered passive device paddle 500 may be between about 0.8 mm$^2$ and about 60.0 mm$^2$. The wirelessly powered passive device paddle 500 also may include spacers between the four electrodes. The spacing between the electrodes may be between about 1 mm and about 6 mm from distal end 512 to proximal end 514.

The various wirelessly powered passive devices described herein may include anywhere from two to sixteen electrodes, any of which can be designated by the programmer as either a cathode or an anode. For example, electrodes can include multiple cathodes coupled to the targeted tissue as well as at least one anode. As illustrated, electrodes 508A and 508B are cathodes while electrodes 510A and 510B are anodes.

The electrode array can receive electrical stimulation waveform pulses ranging from 0 to 10V peak amplitude at a pulse width reaching up to a maximum of 1 millisecond. The polarity of the electrodes can produce various volume conduction distributions from the cathodes to the anodes to inhibit or excite surrounding nerve tissue, which may include A-δ and/or primary or secondary c-fiber afferents. To reduce electrode impedance, the electrodes may be made of a conductive, corrosion resistant, biocompatible material such as, for example, platinum, platinum-iridium, gallium-nitride, titanium-nitride, or iridium-oxide.

The electrodes in the various wirelessly powered passive devices described herein can be made using any conductive, biocompatible material. Examples of suitable materials include metals, alloys, conductive polymers, conductive carbon, and the like, as well as combinations thereof. The electrodes may be typically enclosed in a non-conductive, biocompatible material including, for example, silicone, polyurethane, polyetheretherketone (PEEK), epoxy, and the like or combinations thereof.

Electrodes are coupled to the surrounding tissue. But the remaining portions of the wirelessly powered passive devices described herein may be insulated from surrounding body tissue, at least in part, by an external coating layer of biocompatible dielectric material with a low dielectric constant. Materials with rigidity similar to that of tissue can be used to reduce the risk of migration and the development of fibrous scar tissue. Such fibrous scar tissue can increase electrode-tissue impedance. If the electrode-tissue impedance can be kept low, less energy may be consumed to achieve stimulation of the targeted tissues.

The wirelessly powered passive devices may be formed in the desired shape by any process including, for example, molding (including injection molding), casting, and the like. The non-conductive material typically extends from the distal end of the device to the proximal end. The paddle portion and the device body may be a unitary structure or can be formed as two separate structures that are permanently or detachably coupled together. The wirelessly powered passive device paddle 500 may include antenna 502, rectifier 504, and charge balance circuit 508. Antenna 502, rectifier 504, and charge balance circuit 506 may be housed in device body. Antenna 502 may be configured to receive RF power through electrical radiative coupling and non-inductively from a source external to the device 500. As discussed herein, the electric radiative coupling is a form of non-inductive coupling. This coupling can allow such wirelessly powered passive devices to produce electrical currents capable of stimulating nerve bundles without a physical connection to an implantable pulse generator (IPG) or use of an inductive coil.

For context, RF wave propagation energy is divided into two regions, the radiative region and the reactive region. The radiative region is within $2D^2/\lambda$ and the radiated power varies with distance from the antenna. For a short dipole antenna, the reactive component is approximately $\lambda/2\pi$. The induced field for antennas placed in biological tissue is a function of body geometry, tissue properties, and the exposure conditions. The efficiency of the RF waveform inside a lossy media, such as body tissue, is attenuated by the tissue as it propagates. To increase the power efficiency of a small antenna in lossy matter, the dipole antenna configuration can be optimized at high frequencies to minimize losses, such as, for example, from about 800 MHz to 5.8 GHz or greater.

In some instances, this electrical radiative coupling mechanism (for example, a dipole antenna) can be utilized to improve the form factor of the wirelessly powered passive device and allow for miniature diameters. Electrical radiative coupling may also allow for the transmission and reception of energy at greater depths with less degradation in efficiency than inductive coil techniques. This electrical radiative coupling can provide an advantage over devices that employ inductive coupling where the efficiency of such implants may be highly dependent on the distance separating the external transmitter coil and the implanted receiver coil.

Accordingly, some implementations disclosed herein do not include inductive loops to receive RF energies in a wireless manner. Instead, some implementations disclosed herein use electric radiative coupling to receive RF energies. Such implementations facilitate a smaller form factor for a fully functional implantable electrical stimulation or recording device. The improved form factor may result in a less invasive surgical procedure for placement of the device. The improved form factor may also decrease scarring the amount of bodily tissue in contact with the implanted device is reduced.

The antenna 502 can include, for example, a dipole antenna. Some configurations may have only one dipole antenna; other configurations may have multiple antennas of any given length. For example, without limitation, some configurations may have between two and ten dipole antennas, while other embodiments can have more than ten dipole antennas or more than twenty dipole antennas. In some examples, a dipole antenna can range from about 100 microns to about 10 cm in length. In other examples, an antenna can consist of any linear dipole configuration ranging from about 20 microns to about 3 mm in thickness. The antenna may also be a folded dipole antenna instead of a straight dipole antenna. In some implementations, antenna 502 may include internal dipole (or other) antenna configuration(s) to receive RF power through electrical radiative coupling. In some implementations, at least one of the antennas can be constructed as a conductive trace feature contained on one of the circuits. In other implementations, at least one of the antennas can be fabricated as a conductive wire connected to one of the circuits.

In some implementations, antenna 502 may be coupled to tissue through the antenna coupling contacts located on the ventral side of the wirelessly powered passive device paddle 500. In some implementations, the antenna coupling contacts may have a longitudinal length between about 0.25 mm and about 6.0 mm from the distal tip toward the proximal tip and a width of between about 0.25 mm to about 2.5 mm. The spacing between the antenna coupling contacts may be between about 10 mm and about 80 mm. The antenna coupling contacts may improve the efficiency of the radiative coupling between internal antenna and the antenna(s) located externally to the body. The antenna coupling contracts may be made of noncorrosive metals, such as, for example, platinum, platinum-iridium, gallium-nitride, titanium-nitride, or iridium-oxide.

Antenna coupling contacts may be connected by conducting wires to the antenna(s) and the internal circuitry. The internal circuitry may include, for example, electronic components such as diodes, resistors and capacitors. The internal circuitry uses the incoming energy to provide excitation pulses to the electrodes for excitation of nerve tissue. In some configurations, frequencies from about 300 MHz to about 5.8 GHz, preferably from about 800 MHz to about 2.5 GHz, may be received by the implanted antenna. The excitation pulses released into the tissue from the electrodes may be rectified to provide waveforms at lower frequencies, e.g., at typically from about 5 Hz to about 1000 Hz, but optionally as high as 20,000 Hz.

The wirelessly powered passive device internal circuitry may include rectifier 504, and charge balance circuit 506. In some implementations, the circuitry may include a current limiter, a controller, and an electrode interface.

Rectifier 504 may rectify the signal received by the one or more non-inductive antennas. In one configuration, the internal circuitry may include one or a plurality of diodes as rectifier 504. The diode(s) may rectify the received RF energy received at antenna 502 non-inductively, for example, as sinusoidal signals. The diodes have a low threshold voltage to increase the energy used for creating waveforms and power. In some instances, the rectified signal may be routed to a controller for decoding instructions encoded in the received RF energy.

Additionally, the wirelessly powered passive device internal circuitry may include a charge balancing circuit 506 to reduce or prevent corrosion as well as a current limiter. The charge balance component may be configured to create one or more electrical pulses such that the one or more electrical pulses result in a substantially zero net charge (that is, the pulses are charge balanced). The charge-balanced pulses may be passed through the current limiter to the device interface, which applies the waveforms to the device.

A telemetry signal may be transmitted by the wirelessly powered passive device 500 to deliver information to an external controller. The telemetry signal may be sent by modulation of a carrier signal. The telemetry signal does not interfere with the input received to power the wirelessly powered passive device. In one example, the telemetry signal and powering signal are combined into one signal, where the RF telemetry signal is used to modulate the RF powering signal, and thus the implanted device is powered directly by the received telemetry signal; separate electronic subsystems harness the power contained in the signal and interpret the data content of the signal. In other embodiments, the telemetry output rate is at least 8 kilobits per second.

In other implementations, a RF pulse generator system, located externally to the miniature implanted lead 500, may store parameters defining the excitation pulses to be applied at electrodes, which are transmitted via the second antenna.

Figure 5B:
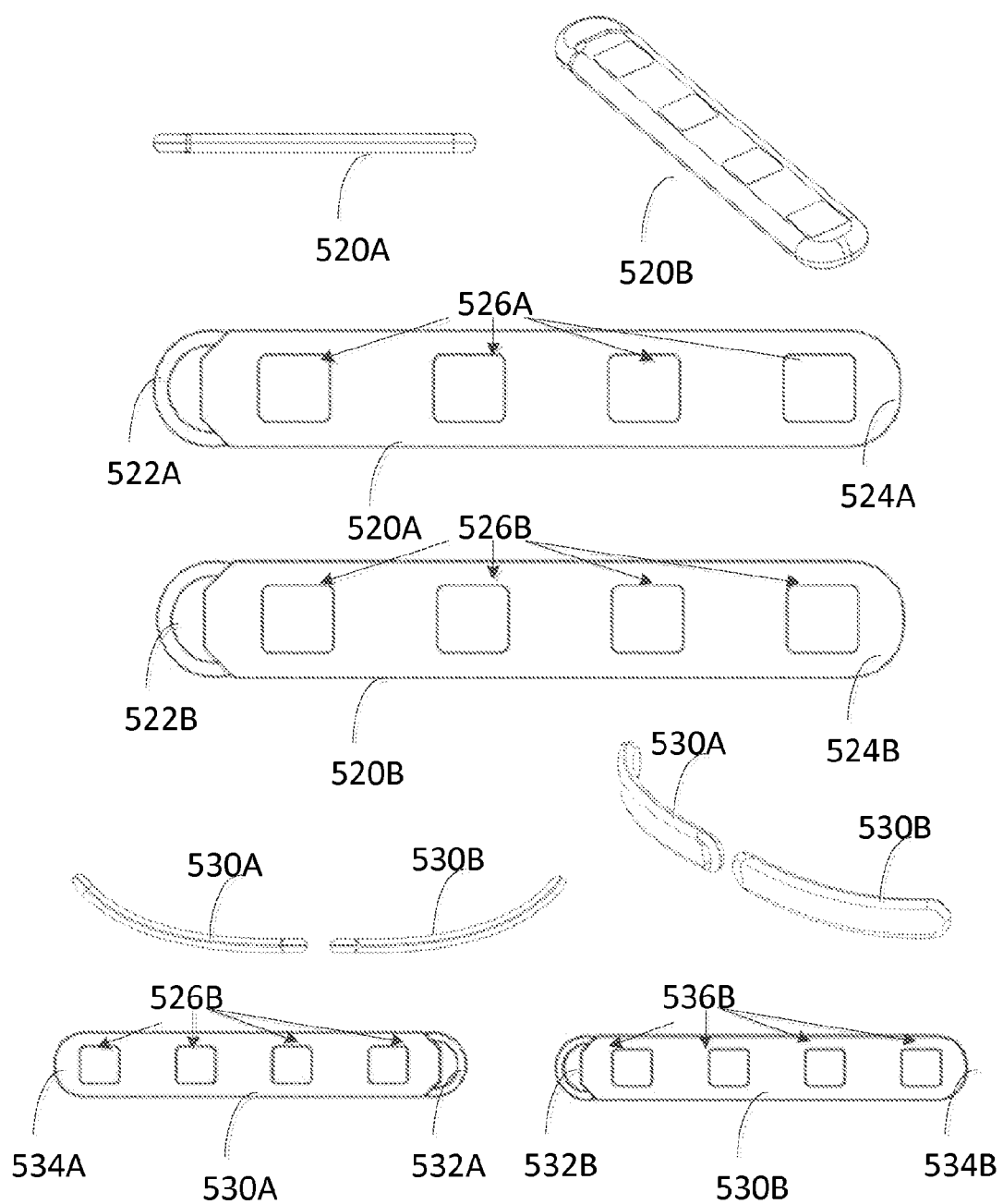
FIG. 5B depicts additional examples of a wirelessly powered passive device paddle form factor.

FIG. 5B illustrates various form factors for a subcutaneous wirelessly powered passive device paddle. As illustrated, the wirelessly powered passive device paddle 520A and 520B each may include respective distal ends 524A and 524B. The distal end may have a height of between about 1.3 mm and about 2.0 mm, and a width between about 2.0 mm and about 4.0 mm. In some implementations, the wirelessly powered passive device paddle 520A and 520B each can have a rounded tip at respective distal end 520A and 520B. The rounded tip preferably comprises a non-conductive, biocompatible material and can have a length of between 0.5 mm and 2.0 mm, and a smooth finish for navigating the wirelessly powered passive device through the appropriate space. In other implementations the wirelessly powered passive device paddle 520A and 520B each can have a pointed tip at respective distal end of the device 520A and 520B. The pointed tip preferably comprises a non-conductive, biocompatible material and can have a length of between about 2.0 mm and about 6.0 mm. The pointed tip can enhance the steering capability when the wirelessly powered passive device paddle is being deployed.

The wirelessly powered passive device paddle 520A and 520B each may include respective proximal ends 522A and 522B. The respective proximal ends 522A and 522B of wirelessly powered passive device paddle 520A and 520B may include a round subcutaneous suture feature that may extend from the proximal tip between about 1.0 mm and 4.0 mm. The wall thickness of the suture feature may be between 0.5 mm and 1.0 mm. The total length of the wirelessly powered passive device paddle may be from between 10 mm to 600 mm.

Wirelessly powered passive devices 520A and 502B are devices with a flat profile. Like the wirelessly powered passive device 500 in FIG. 5A, both devices 520A and 520B also include respective electrodes 526A and 526B.

In comparison, wirelessly powered passive devices 530A and 530B have a curved profile. Otherwise, devices 530A and 530B have similar components to the devices shown in 520A and 520B. As illustrated, both devices 530A and 530B include respective distal ends 534A and 534B with rounded tips for easy placement. The respective distal ends 534A and 534B can include pointed tip as discussed above. Both devices 530A and 530B include respective proximal ends 532A and 532B with suturing features to anchor the respective devices to surrounding tissue. Both devices 530A and 530B also include respective electrodes 536A and 536B.

The table below lists some example materials for various components of the wirelessly powered device as disclosed herein.

| Component | Material | Material Contacts Human Tissue |
|---|---|---|
| Lead | | |
| Flexible Board | Polyimide | No |
| Flexible Circuit Trace | Gold/Copper | No |
| Electrodes | Platinum-Iridium | Yes |
| Insulation | Polyurethane | Yes |
| Cables | MP35N | No |
| Lead Tip | Polyurethane | Yes |
| Adhesive | Silicone | Yes |
| Anchor | | |
| Suture Sleeve Cap | Silicone | Yes |
| Sleeve Cap | Silicone | Yes |
| Guide Wire | Stainless Steel | Yes |
| Stylets (curved, straight) | | |
| Handle | Polypropylene | Yes |
| Wire | Stainless Steel | Yes |
| Stylet Sheath | Pebax | Yes |
| Antenna | | |
| Conductor | MP35N | No |

All implantable materials are medical grade and have been properly handled in a clean room setting. Prior to distribution, materials can be sterilized using low temperature methods such as ethylene oxide, gamma, or e-beam.

Figure 6:
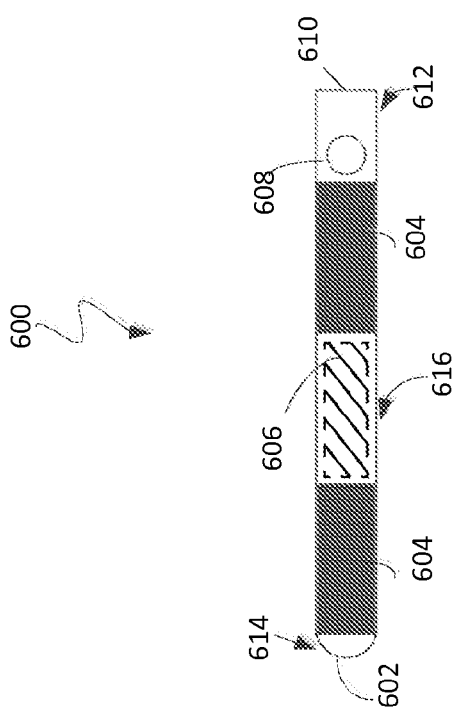
FIG. 6 illustrates an example of a miniature implantable device including wireless power receiving electronics.

FIG. 6 illustrates an example miniature implantable device 600. The implantable device 100 includes a body 616 with a distal end 614 and a proximal end 612.

The distal end 614 includes a rounded tip 602. The distal end 614 of the miniature wireless device body 616 may include a non-conductive tip 602 that is rounded with a length of between about 0.5 mm and about 1.0 mm, with a smooth finish for navigating the device through tissue.

The device body 606 includes electrodes 604 and houses electronic circuitry 606. In some implementations, the miniature implantable device may have between one and twenty-four cylindrical electrodes 604 on its distal end 614 with a diameter between about 0.1 mm and about 0.8 mm for stimulation applications. The diameters and other sizes may, of course, vary from one target treatment to another target treatment. The electrodes 604 may have a longitudinal length of between about 0.25 mm and about 6.0 mm from the distal end 614 toward the proximal end 612. The spacing between the electrode contacts may be between about 0.25 mm and about 6.0 mm. The total electrode surface area of the cylindrical wireless lead body may be between about 0.06 mm$^2$ and about 250.0 mm$^2$.

The proximal end 612 includes a suturing feature 608 and a mating feature 610. The suturing feature 608 is a passage through the proximal end with a central axis that is parallel to a longitudinal axis of the device body 606. Suturing feature 608 may allow a clinician to suture and anchor implantable device 600 during an implantation procedure. For instance, suture can be passed through the passage of suturing feature 608 and tied to tissue. In some cases, the implantable device 600 can be sutured to the surrounding tissue. Suturing the implantable device may reduce mobility and improve stability of the implanted device.

Mating feature 610 may allow the device 600 to be mechanically mated with a stylet, as disclosed herein. In one configuration, mating feature 610 is a concave indentation that extends along a longitudinal axis of the device body 106 from the proximal end 612. The concave indentation mates with a corresponding feature on a placement stylet or suction stylet. The concave stylet-mating feature on the proximal end 610 of implantable device 600 can have, for example, a length of between about 0.1 mm and 1.0 mm. In other configurations, the stylet-mating feature 610 may be semi-spherical or asymmetrical in shape for improved steerability of the device during implantation.

The various devices described herein, including device 600, may include, for example, anywhere from one to twenty-four electrodes 604, any of which can be designated by a programmer user as either a cathode or an anode. For example, electrodes 604 can include multiple cathodes coupled to the targeted tissue as well as at least one anode. The electrode array can receive electrical stimulation pulses ranging from about 0 to about 10 V peak amplitude at a pulse width up to about 1 millisecond. Such stimulation pulses may be from a single receiver element within the device body. The polarity of the electrodes can produce various volume conduction distributions from the cathodes to the anodes to inhibit or excite surrounding excitable tissue, which may include A-δ and/or primary or secondary c-fiber afferents. To reduce electrode impedance, the electrodes may be made of a conductive, corrosion resistant, biocompatible material such as, for example, platinum, platinum-iridium, gallium-nitride, titanium-nitride, or iridium-oxide.

The miniature implantable device 600 may be 0.8 mm diameter or smaller. Miniature implantable device 600 may receive microwave or RF energy from an external source non-inductively and without a wire. The miniature implantable 100 device may contain the circuitry necessary to receive the pulse instructions from a source external to the body.

In particular, electronic circuitry 606 of the miniature implantable device may convert an input signal received at the one or more antennas into an electrical energy and electrical pulses. In some implementations, extension tubing can provide an enclosure that houses, for example, flex circuitry. In some embodiments, the electronic circuitry 106 may include one or a plurality of diodes that function to rectify the wireless signal, such as a sinusoidal signal, picked up by the non-inductive antenna(s). The diodes have a low threshold voltage to maximize the energy used for creating waveforms and power. Additionally, internal circuitry 106 may include a charge balancing microelectronic component to reduce or prevent corrosion as well as a current limiter.

In certain embodiments, the electronic circuitry 606 may include one or more non-inductive antennas, a rectifier, a charge balancer, a current limiter, a controller, and a device interface. In brief, the rectifier functions to rectify the signal received by the one or more non-inductive antennas. The rectified signal may provide power to electrodes 604. The rectified signal may also be fed to a charge balance component that is configured to create one or more electrical pulses such that the one or more electrical pulses result in a substantially zero net charge (that is, the pulses are charge balanced). The charge balanced pulses are passed through the current limiter to the electrode interface, which applies the electrical pulses to electrodes 604.

In some implementations, an internal dipole (or other) antenna configuration(s) may be used in lead 100 to receive RF power through electrical radiative coupling. This coupling mechanism can allow such devices to produce electrical currents capable of stimulating nerve bundles without a physical connection to an implantable pulse generator (IPG) or use of an inductive coil. In some implementations, between two to eight tissue-exposed-ring-antenna coupling contacts may be proximal to the electrodes. The tissue-exposed-ring-antenna coupling contacts may have a longitudinal length of between about 0.25 mm and about 6.0 mm from the distal end 614 toward the proximal end 610. The spacing between the tissue-exposed ring antenna coupling contacts may be between about 5 mm and about 80 mm. In certain implementations, tissue-exposed-small-antenna coupling contacts with a diameter between about 0.2 mm and about 0.6 mm may be used in lieu of the tissue-exposed-ring-antenna coupling contacts.

In some implementations, at least one of the antennas can be constructed as a conductive trace feature contained on one of the circuits. In other implementations, at least one of the antennas can be fabricated as a conductive wire connected to one of the circuits. In various implementations, implantable device 600 my employ non-inductive, for example, dipole or other antenna configuration(s), to receive RF power through electrical radiative coupling.

For context, neural stimulating devices may utilize a battery-powered or charge-storage component. Such devices are no longer functional once the battery cannot be recharged or charge cannot be stored. Consequently, for an implanted device, a patient would need to undergo a subsequent surgical procedure to obtain a functional replacement device.

In contrast, some implementations disclosed herein do not rely upon battery power or charge storage for operation. In some configurations, the implantable device can receive electrical power from radiated RF energy non-inductively and without a wired connection. As a result, the life of an implanted device is no longer limited by the life of the battery or ability to store charge.

Further, the electrical radiative coupling mechanism (for example, a dipole antenna) can be utilized to improve the form factor of the miniature implanted device and allow for miniature diameters. Electrical radiative coupling may also allow for the transmission and reception of energy at greater depths with less degradation in efficiency than inductive coil techniques. This electrical radiative coupling can provide an advantage over devices that employ inductive coupling where the efficiency of such implants may be highly dependent on the distance separating the external transmitter coil and the implanted receiver coil.

Accordingly, some implementations disclosed herein do not include inductive loops to receive RF energies in a wireless manner. Instead, some implementations disclosed herein use electric radiative coupling to receive RF energies. Such implementations facilitate a smaller form factor for a fully functional implantable electrical stimulation or recording device. The improved form factor may result in a less invasive surgical procedure for placement of the device. The improved form factor may also decrease scarring the amount of bodily tissue in contact with the implanted device is reduced.

A telemetry signal may be transmitted by the miniature implantable device 100 to deliver information to an external controller. The telemetry signal may be sent by modulation of a carrier signal. The telemetry signal does not interfere with the input received to power the miniature implantable device. In one example, the telemetry signal and powering signal are combined into one signal, where the RF telemetry signal is used to modulate the RF powering signal, and thus the implanted device is powered directly by the received telemetry signal; separate electronic subsystems harness the power contained in the signal and interpret the data content of the signal. In other embodiments, the telemetry output rate is at least 8 kilobits per second.

In other implementations, a RF pulse generator system, located externally to the miniature implanted device 600, may store parameters defining the excitation pulses to be applied at electrodes 604, which are transmitted via the second antenna.

Figure 7:
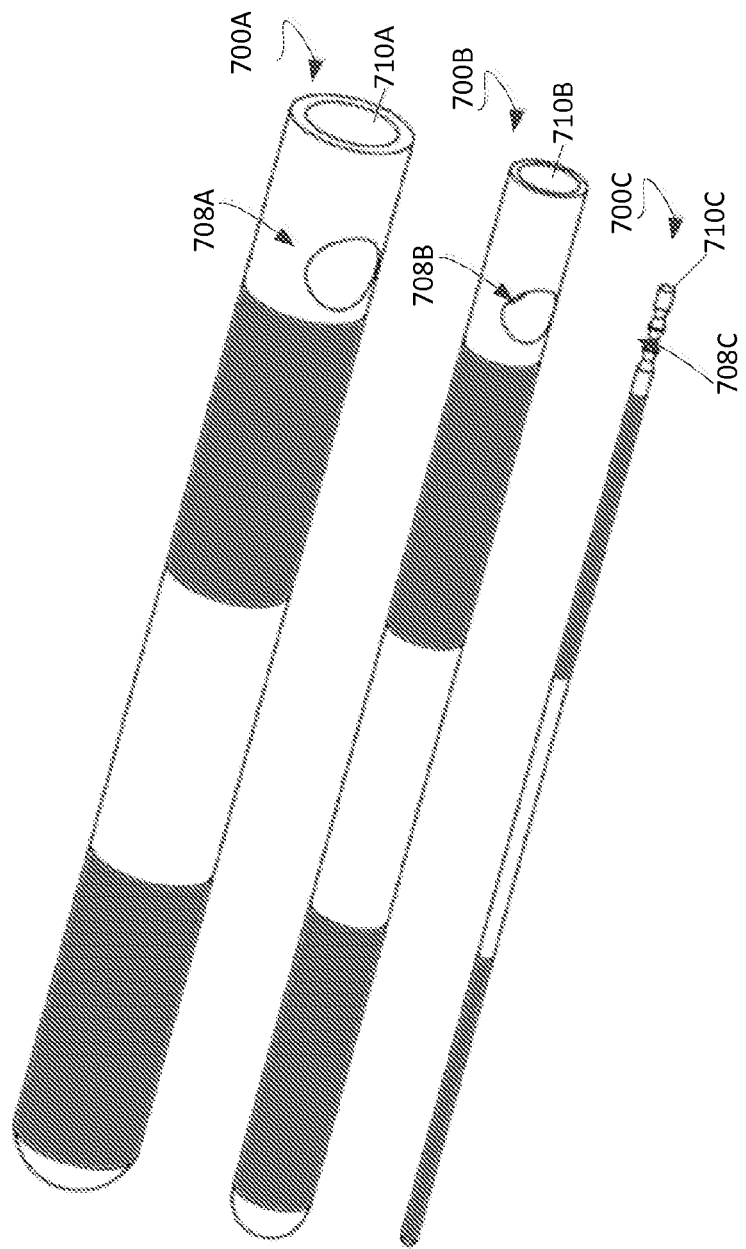
FIG. 7 shows three different sized miniature implantable devices.

FIG. 7 illustrates three examples of miniature implantable devices 700A, 700B, and 700C with various diameters. Miniature implantable device 700A is a miniature implantable device with a diameter of 0.8 mm. Miniature implantable device 700A includes a suturing feature 708A to allow a clinician to suture and anchor implantable miniature implantable device 700A during an implantation procedure. For instance, suture can be passed through the passage of suturing feature 708A and tied to tissue such that the mobility of the implanted device is reduced. As illustrated, implantable device 700A also includes an indentation 710A on the proximal end to allow for mating with a placement stylet during implantation.

Miniature implantable device 700B has a diameter of 0.4 mm and has a suturing feature 708B similar to 708A. Implantable device 700B also includes an indentation 710B on the proximal end to allow for mating with a placement stylet during implantation.

Miniature implantable device 700C has a diameter of 0.1 mm. Miniature implantable device 700C includes a suturing feature 708C in the form of ribs to aid suture in attaching to a surrounding tissue. Implantable device 700C also may include an indentation 710C to allow for mating with a placement stylet during implantation.

Figure 8:
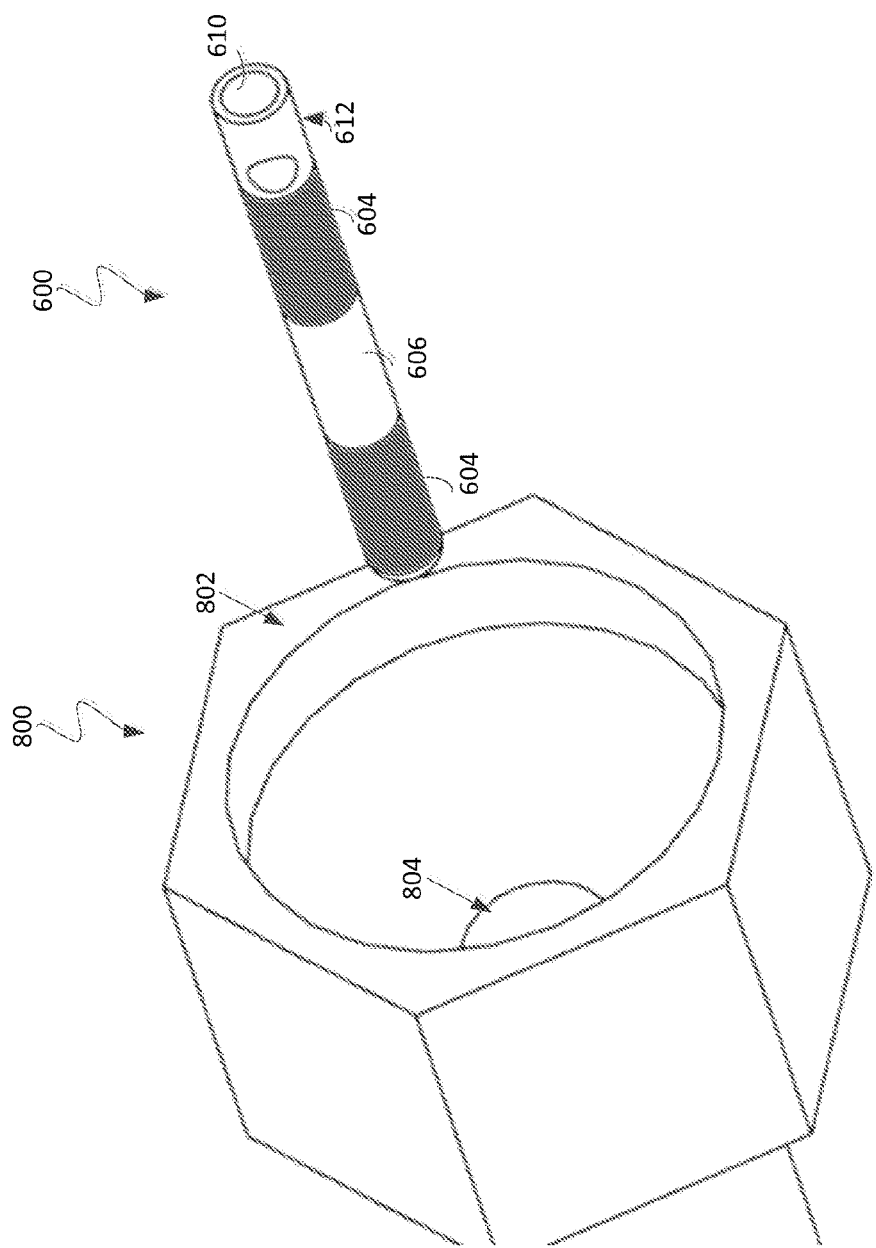
FIG. 8 illustrates a miniature implantable device entering an introducer needle.

FIG. 8 illustrates the miniature wireless device 600 (e.g., a 0.8 mm diameter) entering an 18 gauge needle 800. The distal end (not shown) of miniature implantable device is in position to enter the proximal opening 802 of an 18-gauge needle 800. Miniature implantable device 600 has a diameter small enough to fit into the inner lumen 804 of the needle 800. The illustration may correspond to an implantation of a miniature implantable device with a diameter of 0.8 mm, shown as the implantable device 700A in FIG. 7. Notably, the middle and bottom devices (0.4 mm and 0.1 mm, respectively) shown in FIG. 7 are sized for advancement through introducer needles with even smaller sizes, (e.g., 22 gauge or smaller).

While it is possible to place the device 600 directly into an introducer needle, doing so may not be desirable as the implantable device enclosure may not be as rigid as a guide wire and may not slide easily within the inner lumen of the introducer needle. Yet, a guide wire may not be used because the implantable device may not have a central void through which to mount the guide wire. To improve the ease of placement through an introducer needle, a stylet may be used to provide some rigidity to the miniature device.

Figure 9A:
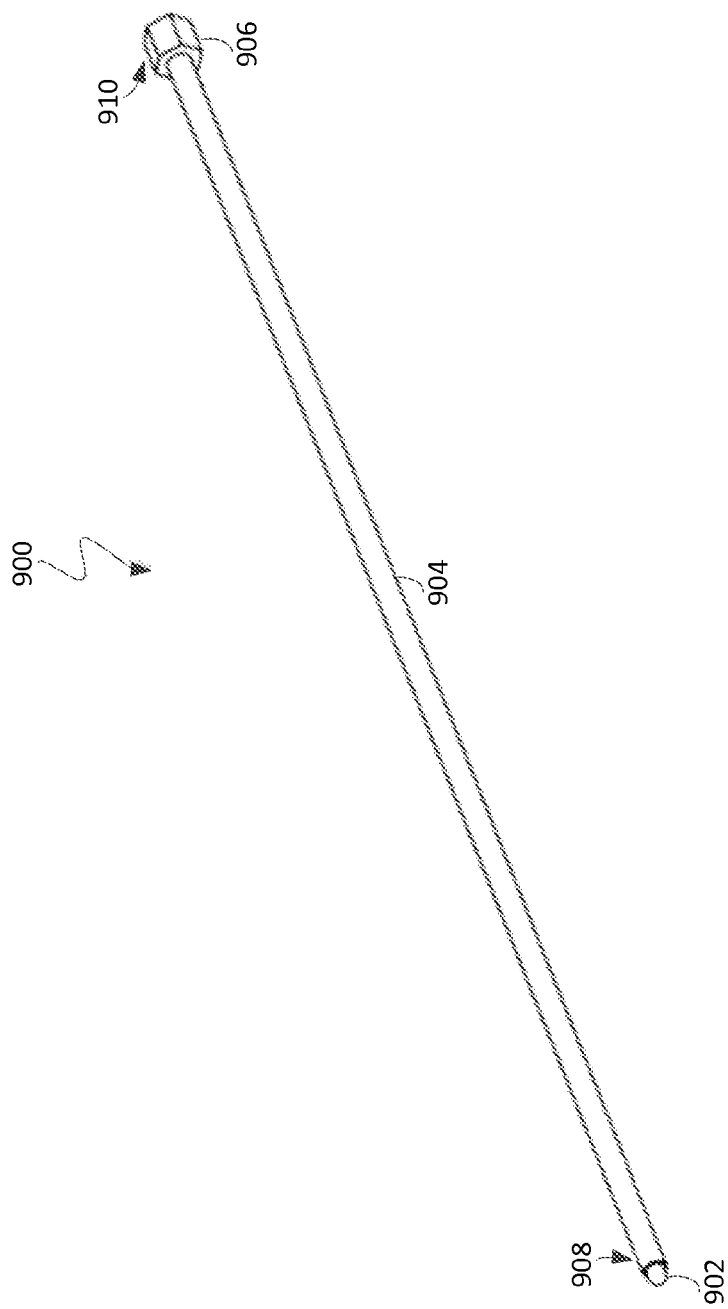
FIG. 9A shows a placement stylet capable of mating with a miniature implantable device.

FIG. 9A shows a placement stylet 900 capable of mating with a miniature implantable device 600 according to some implementations. Placement stylet 900 includes a distal end 908, device body 904, and proximal end 910. Distal end 908 includes a mating feature 902 to allow the placement stylet 900 to engage, for example, miniature implantable device 600. The mating feature 902 is, for example, a convex protrusion that is shaped and sized to mate with the concave indentation 610 of the lead 600. Proximal end 906 includes handle 906 for operator to hold placement stylet 900, for example, during an implantation procedure. Placement stylet 400 can have a longitudinal length of between about 50 mm and about 177 mm. Placement stylet 900 can have an outer diameter in the range from between about 0.1 mm and about 0.9 mm. Placement stylet 900 may be made of a rigid biocompatible material such as stainless steel, titanium, nylon, or polyethylene.

Figure 9B:
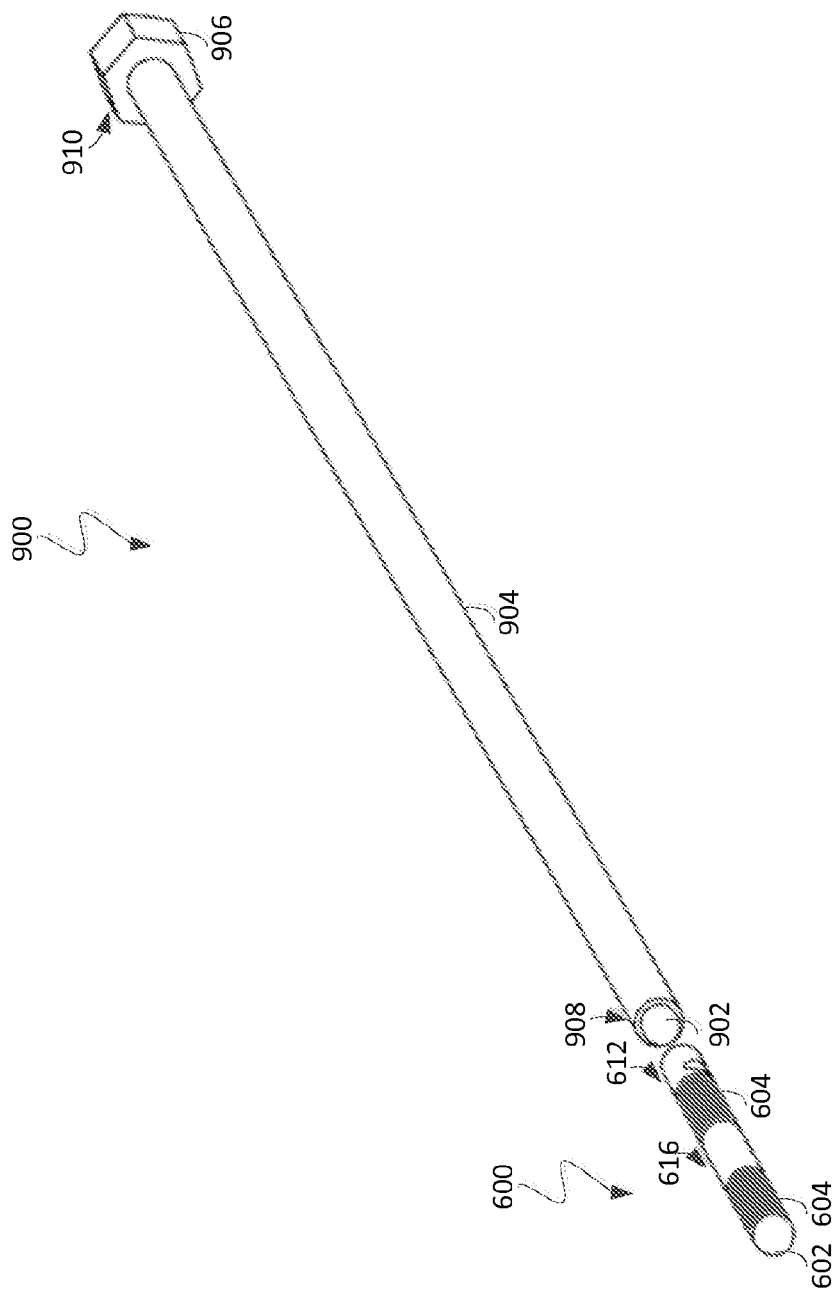
FIG. 9B illustrates a miniature implantable device mated with a placement stylet.

FIG. 9B illustrates a miniature implantable device 600 mated with a placement stylet 900. A clinician may mate the miniature implantable device 600 onto the placement stylet 900. The mating feature 902 on the distal end 908 of the stylet may mate with mating feature 610 on the proximal end 612 of miniature implantable device 600. Mating feature 902 on placement stylet 900 may be semi-spherical in shape, and may provide mechanical gripping for placement stylet 900 to engage the miniature implantable device 600 during placement. Mating feature 902 may be complementary in shape to the shape of mating feature 612 on the proximal end 610 of the device 600. In some configurations, mating feature 902 may be convex in shape. In other configurations, mating feature 902 may include extruded shapes for mating the stylet 900 to the miniature implantable device 600 at mating feature 612, which may have a square, hexagon, star, or an asymmetrical shape. Mating feature 902 may only protrude from the distal end 908 of placement stylet 400 from between 0.1 mm and 1.0 mm and may not fill the entirety of the device body 606 (that is, the feature 902 may only extend partially into device body 606). Mating feature 902 may have a surface material that allows for increased friction to improve the mate between placement stylet 900 and the miniature implantable device 600. Example materials may include silicon or polyurethane.

Figure 10A:
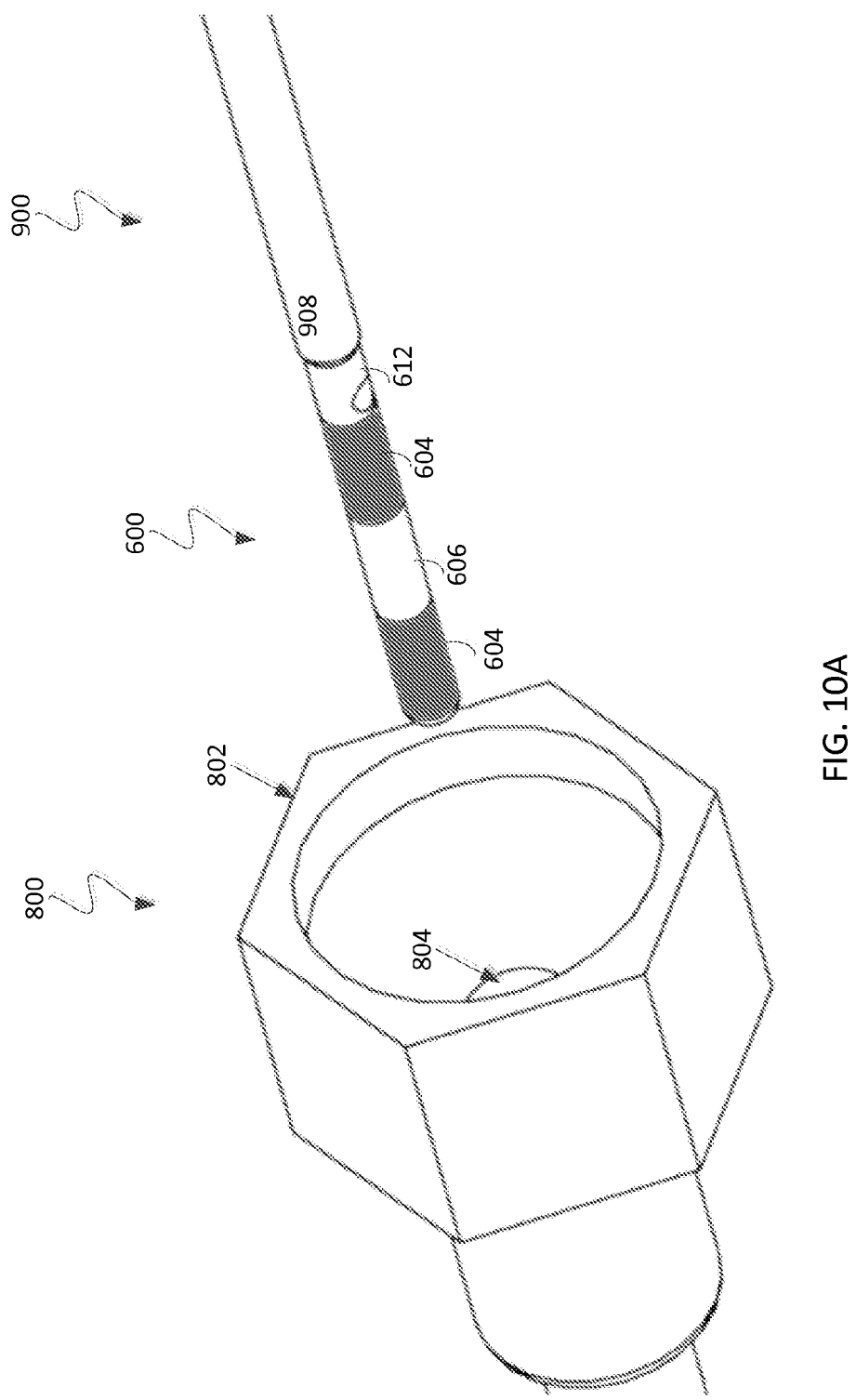
FIG. 10A shows a miniature implantable device mated with a placement stylet entering a proximal opening of an introducer needle.

FIG. 10A illustrates a miniature implantable device 600 mated with a placement stylet 900 entering a proximal opening 902 of needle 800. Miniature implantable device 600 includes lead body 616 that includes electrodes 604 and houses electronic circuitry 606. The proximal end 612 of miniature implantable device 600 is now mated with the distal end 908 of placement stylet 900. As illustrated, after the miniature implantable device 600 has been mated to placement stylet 900, the subassembly of the device 600 with the stylet 900 can now be inserted into an 18 gauge needle 800 or smaller. In particular, the miniature implantable device 600 at the proximal opening 302 of needle 800 is being pushed into position with the placement stylet 900. In fact, the stylet/miniature device subassembly may now slide freely within the inner lumen 304 of the needle 800. The free sliding motion may aid in the surgical placement of the miniature device 600.

Figure 10B:
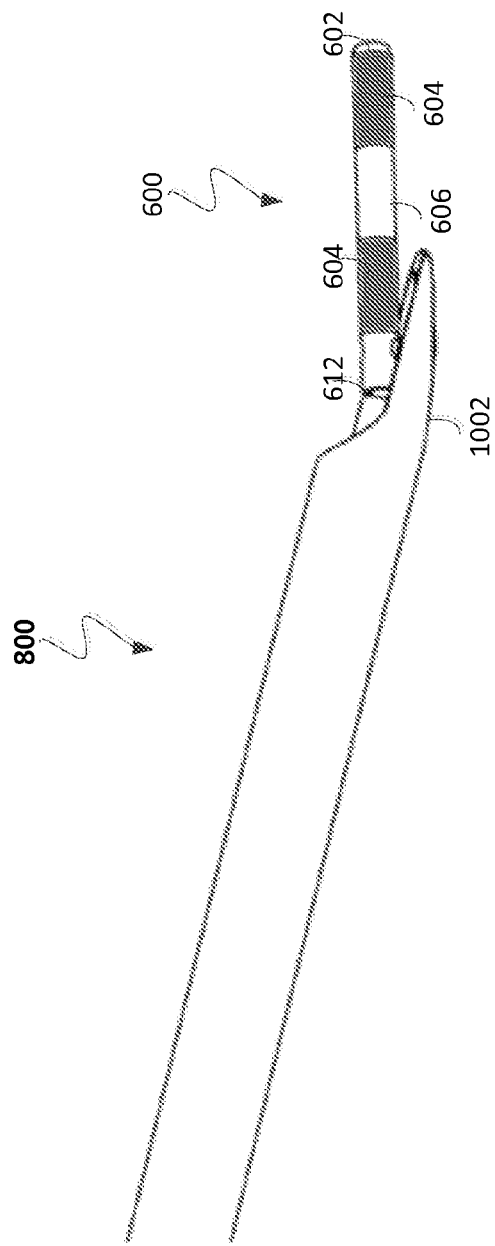
FIGS. 10B and 10C show a miniature implantable device mated with a placement stylet exiting a distal tip of an introducer needle.
Figure 10C:
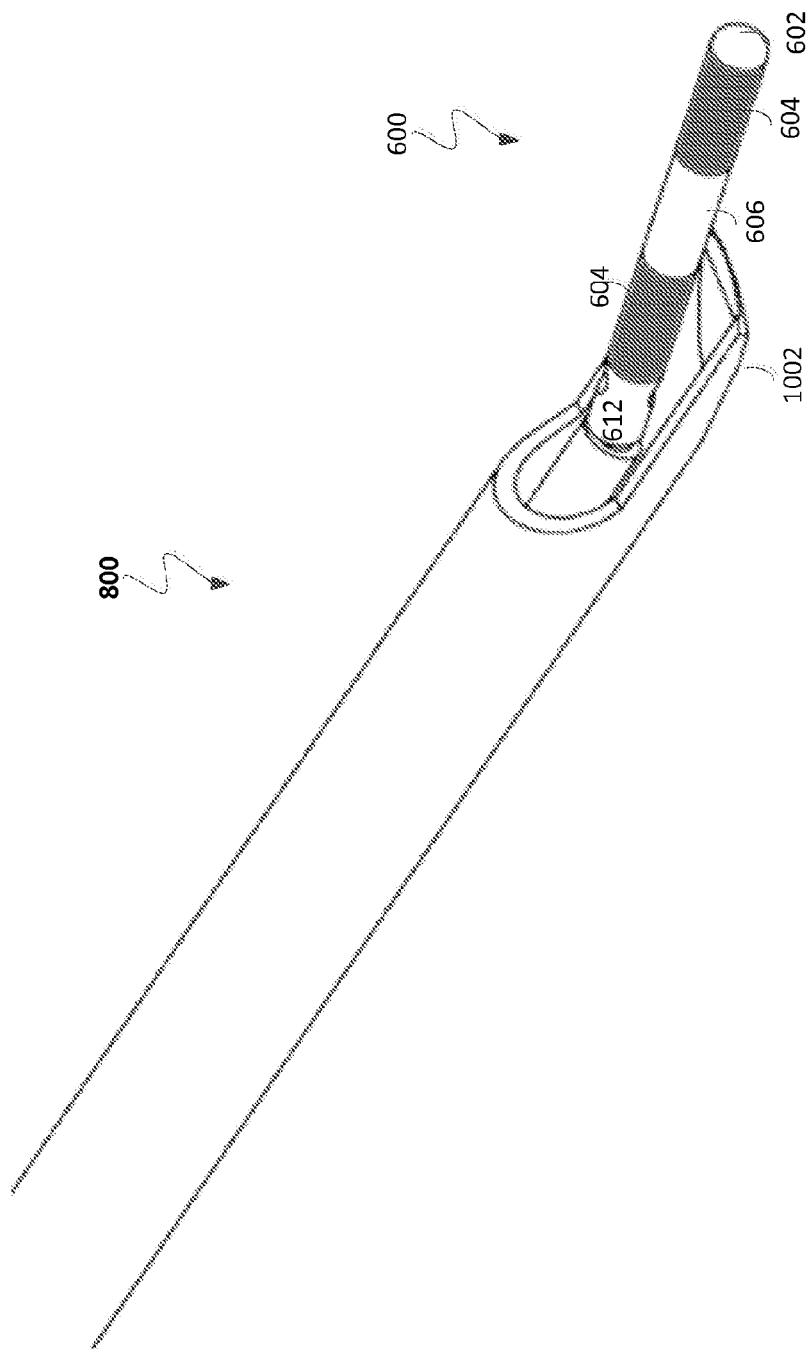

FIGS. 10B and 10C show a miniature implantable device 600 mated with a placement stylet 900 exiting a distal end 902 of needle 800. As discussed above, the miniature implantable device 600 may freely traverse the inner lumen 804 of needle 800 with a size of 18 gauge or smaller. Once the traversal is completed, the miniature implantable device 600 may exit the needle under the pushing force applied on the placement stylet 900 mated to the device 600. As illustrated, rounded tip 602 and body 616 of miniature implantable 600 have exited the distal end 902 of needle 800. The portions of body 616 that include electrodes 604 and electronic circuitry 606 are also shown on FIGS. 10B-10C. The proximal end 612 of miniature implantable 600 is mated to the distal end 908 of placement stylet 900. After the implantable 600 has been placed into a target region, the implantable device 600 may be sutured or anchored in place. Thereafter, the placement stylet 900 may be unmated from the implanted 600. A clinician may then withdraw the placement stylet 900 by pulling the placement stylet 900 out of the patient's body through the needle 900. The placement and withdrawal process may be performed under imaging guidance, such as, for example, X-Ray fluoroscopy, ultrasound fluoroscopy, etc. Once the procedure is completed, needle 800 may be removed.

Figure 11:
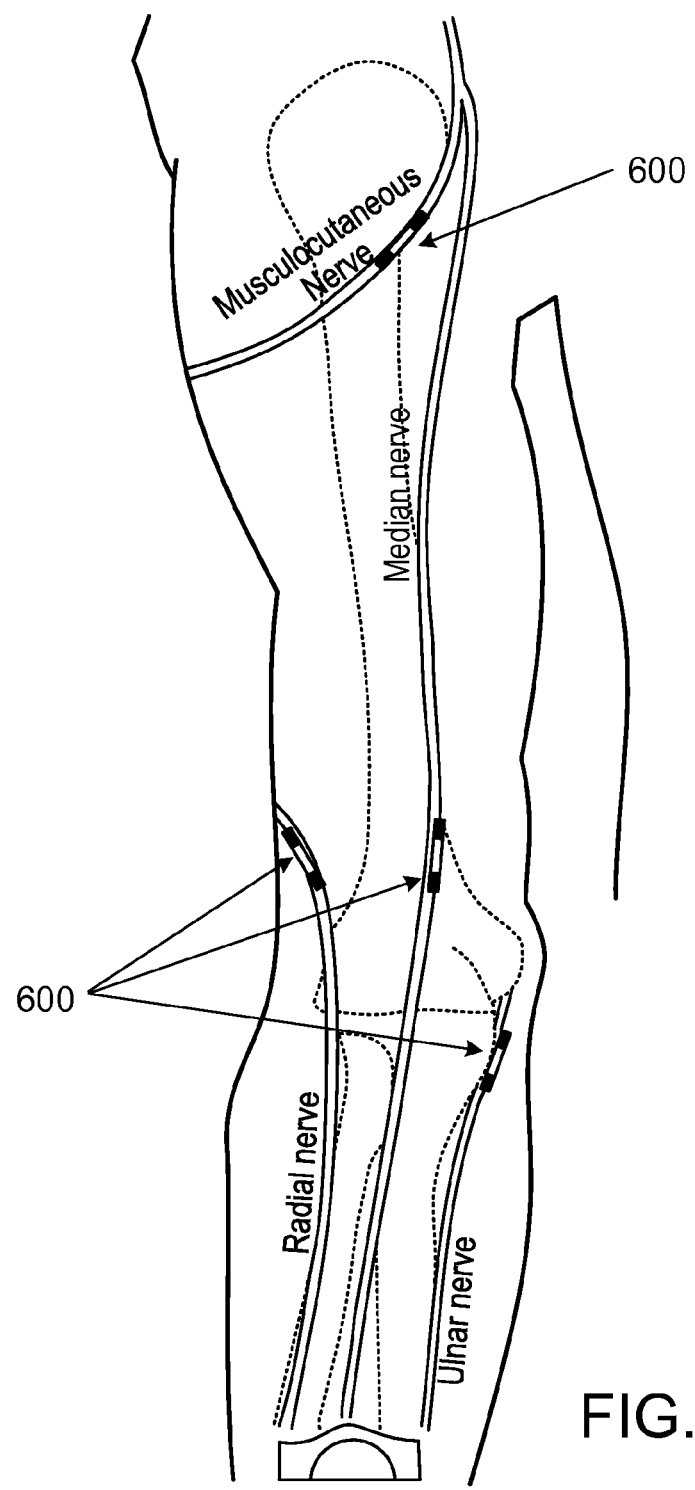
FIG. 11 illustrates the anatomical placement of four miniature implantable devices in the forearm.

FIG. 11 demonstrates the feasibility of placing multiple miniature implantable devices in the anatomical positions of the forearm. The compact size of the miniature implantable device 600 may allow minimally invasive placement procedure, thereby reducing complications during procedure and improving recovery time after procedure. Moreover, the compact size may allow multiple miniature implantable devices to be placed in nearby target areas. As shown in FIG. 11, four miniature implantable devices 600 are placed into the forearm of a patient, one in the upper forearm area and three in the lower forearm area. Each implanted lead may treat a specific nerve branch in the forearm region. Similarly, the miniature implantable devices 600 also may be delivered to treat a neural tissue branching from the spinal column including but not limited to the dorsal root ganglia, traversing, or exiting nerve. The miniature implantable devices 600 may also be delivered to treat peripheral nerve targets such as the radius, ulnar, sciatic, femoral, occipital, or brachial nerves. Given the compact size of the miniature leads, two or more such devices may be placed with pin-point precision to treat multiple nerve branches or peripheral nerve targets at the same time. In particular, two or more such devices may be placed with close proximity within a target area to provide pain-relief therapy to one or more excitable tissues within the target area. For instance, a patient may have one miniature implantable device 600 implanted adjacent to or near a target area. If more therapeutic effect is desired, the patient may have additional miniature implantable devices 600 implanted adjacent to or near the target area to enhance the therapeutic effect.

Figure 12A:
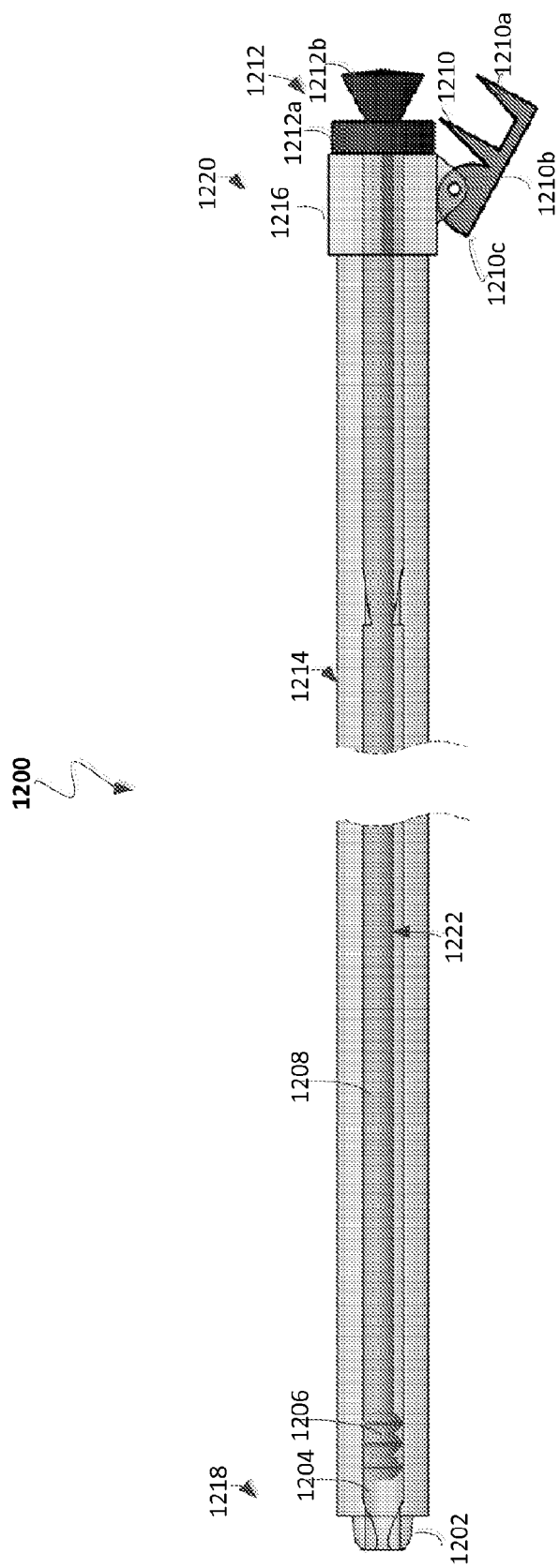
FIG. 12A illustrates an example suction stylet in zero pressure mode.

FIGS. 12A-12E illustrate a suction stylet 1200 in various modes of operation. The suction stylet 1200 is different from the placement stylet 900 described above. As shown in FIG. 12A, the suction stylet 1200 is hollow inside and may have an outer diameter of between about 0.1 mm and 0.9 mm and may have a longitudinal length of between about 50 mm and 170 mm. The suction stylet 1200 may have an inner diameter between about 0.05 mm and 0.75 mm. The suction stylet 1200 includes distal end 1218, stylet body 1214, and proximal end 1216.

The distal end 1218 may include a mating feature 1202, chamber 1204, and plunger tip 1206. Mating feature 1202 also may be referred to as the suction tip. In some configurations, mating feature 1202 may be semi-spherical in shape and may have a diameter between about 0.05 mm and 0.08 mm. Mating feature 1202 on suction stylet 1200 may mate to mating feature 610 on miniature wireless lead 600, in a manner similar to the mechanical mating described above. In some instances, a mating force may be provided by a negative air pressure created inside air chamber 1204 on suction stylet 1200. In particular, by moving the plunger tip 1206 along the shaft for inner plunger 1208, a negative air pressure may be created in chamber 1204.

Stylet body 1214 may include inner plunger 1208 located inside shaft 1222. The inner plunger shaft 1222 may have a diameter between about 0.05 mm and 0.75 mm, allowing the plunger 1208 to slide inside of the hollow suction stylet 1200. The total length of the inner plunger including the inner plunger handle may be between about 50 mm and 170 mm. The inner plunger shaft, when installed, may not protrude beyond the suction tip.

The proximal end 1220 of suction stylet 1200 may include base 1216, handle 1212, and locking feature 1210. Base 1216 may have a diameter of between about 0.1 mm and 0.9 mm depending on the outer diameter of the hollow stylet 1200 being utilized. Handle 1212 may include cap 1212a and tip 1212b. Cap 1212a closes the tubing of suction stylet 1200. Handle tip 1212b may be pulled out during a placement procedure. The pulling may cause sliding motion of the plunger 1208 inside shaft 1222, which creates a negative air pressure in chamber 1204. Suction force may be created on suction tip, mating feature 1202, so that suction stylet 1200 is mated with miniature implantable device 600. Locking mechanism 1210 may include spike 1210a, spike 1210b, and hinge 1210c. Hinge 1210c is mounted on base 1216 and may rotate to engage spikes 1210a and 1210b with cap 1212a, as discussed below.

Figure 12B:
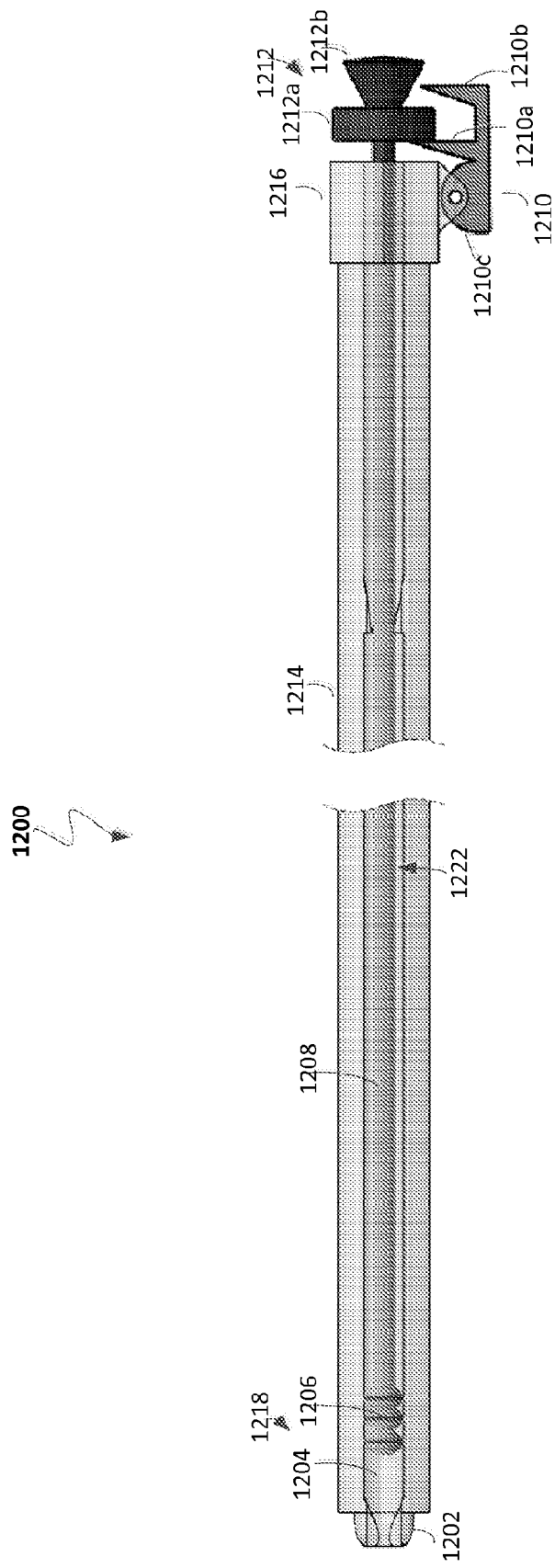
FIG. 12B illustrates the example suction stylet in first level of negative pressure mode.
Figure 12C:
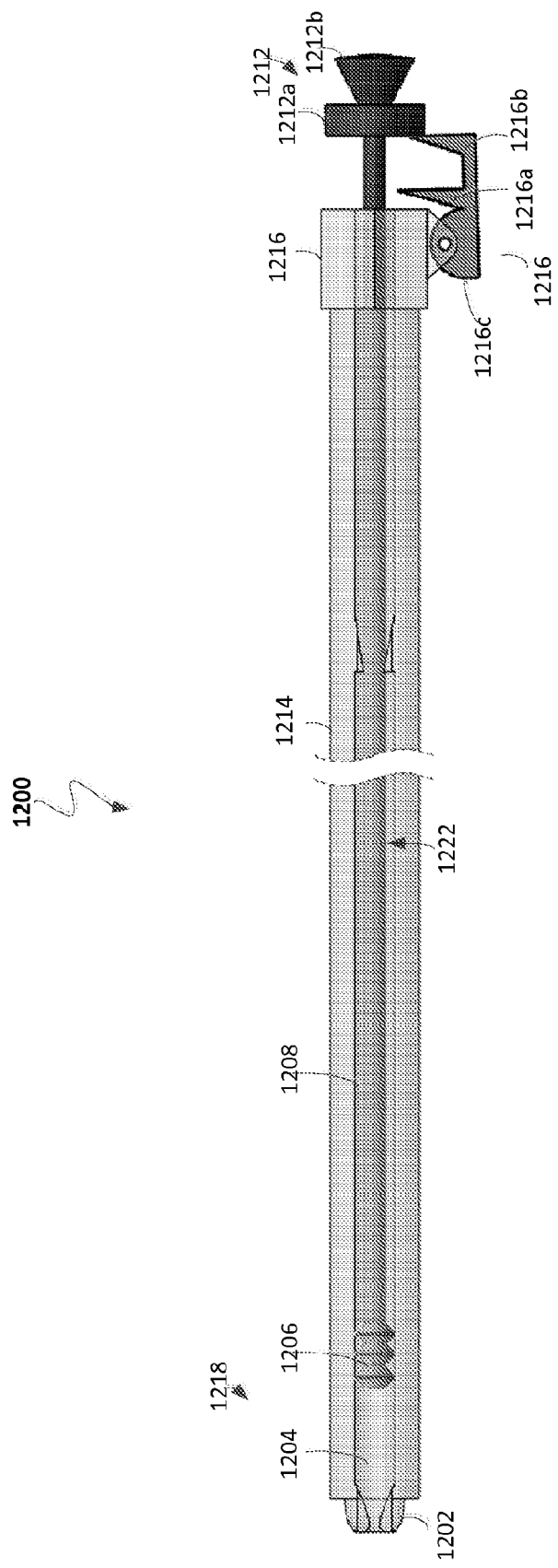
FIG. 12C illustrates the example suction stylet in second level of negative pressure mode.

FIGS. 12A to 12C show the suction stylet without the mating miniature implantable device. As illustrated, the inner plunger 1208 may be slid in a translating motion inside shaft 1222 to different locations within the hollow stylet 1200. Locking mechanism 1210 may be used to lock plunger 1208 into certain positions.

In particular, FIG. 12A shows the inner plunger 1208 in a complete seated condition with respect to the distal end 1220 of stylet 1200. In this position, no pressure differential may exist between the mating feature 1202 and plunger tip 1206.

Figure 12D:
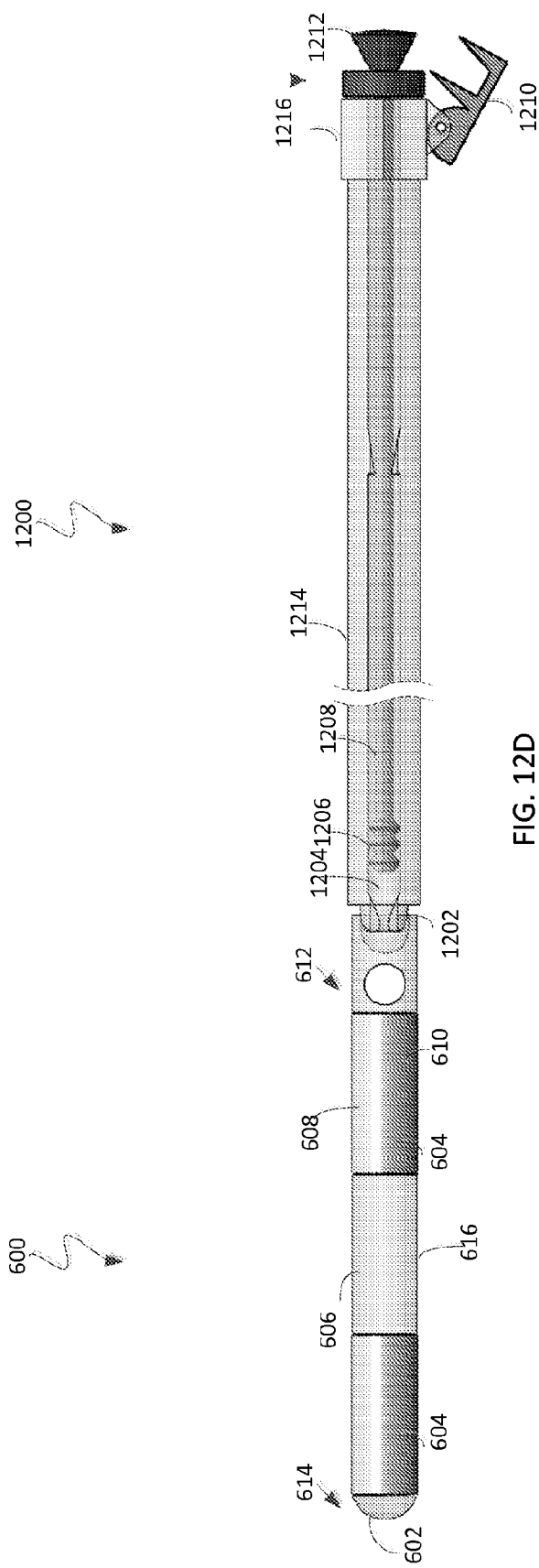
FIG. 12D illustrates an example miniature implantable device when the suction stylet is not active.

FIGS. 7B and 7D shows the inner plunger 1208 at stage 1 position, which may be between about 1 mm and 10 mm from mating feature 1202 (suction tip) of the hollow stylet 1200. FIG. 12B shows suction stylet 1200 without the mated miniature implantable device 600, while FIG. 12D shows suction stylet 1200 mated with miniature implantable device 600. By pulling the handle tip 1212b away from the hollow stylet, a pressure differential may be generated to create a temporary mate between the miniature implantable device 600 and the stylet 600. The mate is between mating feature 602 on miniature implantable device 600 and suction tip 1202 on suction stylet 1200. Locking mechanism 1210, as shown in FIG. 12B, may lock the inner plunger 1208 in place by engaging spike 1210a between base 1216 and cap 1212a. Once locked, the pressure differential between suction tip (mating feature 1202) and plunger tip 1206 may be maintained. This locking mechanism may be adjustable to allow for the inner plunger to be locked in a desired location.

Figure 12E:
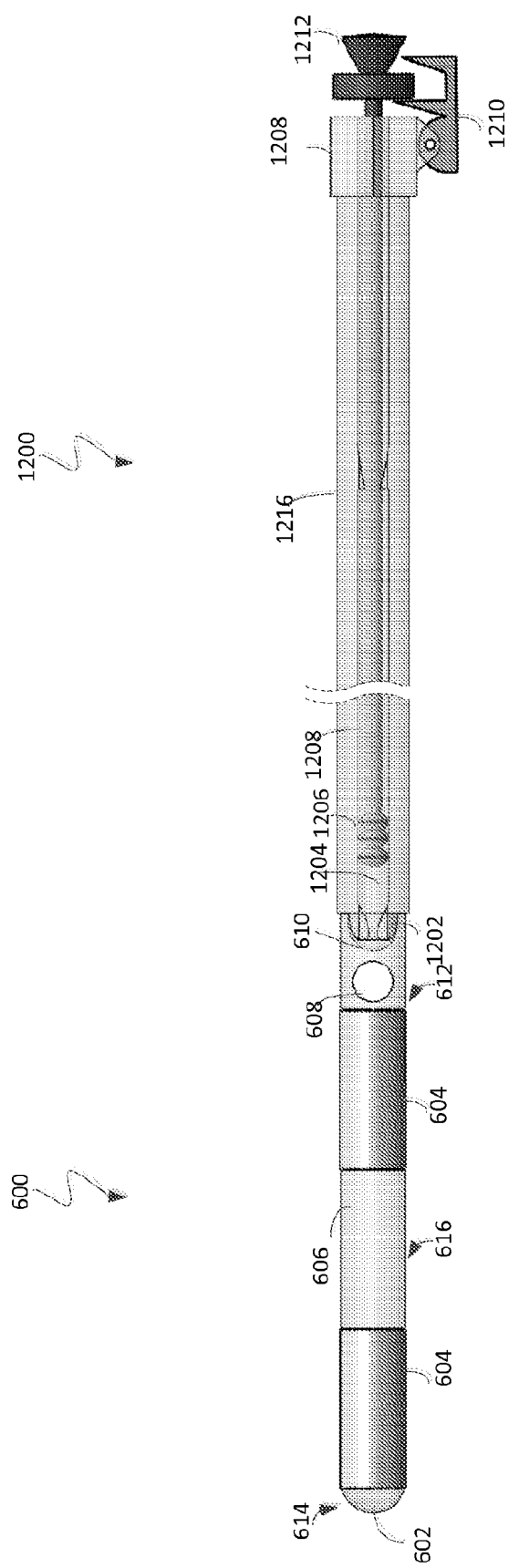
FIG. 12E illustrates an example miniature implantable device when the suction stylet is active.

FIGS. 12C and 12E illustrate the inner plunger 1208 being locked into a stage 2 location, which may be between about 2 mm and 30 mm from mating feature 1202 (suction tip) of the hollow stylet 1200. FIG. 12C shows suction stylet 1200 without the mated miniature implantable device 600, while FIG. 12E shows suction stylet 1200 mated with miniature implantable device 600. This stage may have a greater pressure differential generated than the stage 1 location depicted in FIG. 12B. In other examples, a suction stylet assembly may have one more locking stages depending on the locking mechanism utilized. An adjustable locking mechanism may allow for infinite locking distance locations.

The suction stylet design may provide the clinician the ability to install and remove the miniature implantable device 600 from a patient. As discussed above, once suction stylet 1200 is activated to engage miniature implantable device 600, an assembly of miniature implantable device 600 and suction stylet 1200 may be created. The clinician may push the suction stylet to advance the entire assembly, for example, down the inner lumen 804 of needle 800, towards the target site. If the miniature implantable device 600 is already implanted, the clinician can mate the miniature implantable device 600 to the suction tip of the stylet 1200, then pull on handle tip 1212b. Plunger 1208 may slide inside shaft 1222, thereby creating a pressure differential between suction tip 1202 and plunger tip 1206. The pressure differential may engage the miniature implantable device 600, and the clinician may withdraw the suction stylet 1200 to take the implanted lead 600 from within the patient.

Figure 13A:
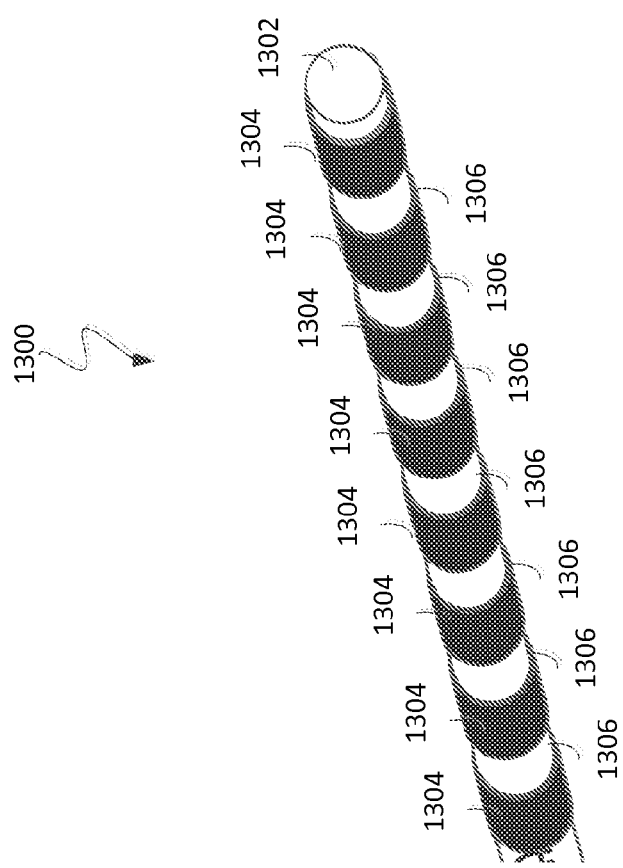
FIG. 13A illustrates a miniature implantable device with multiple recording or stimulating cylindrical electrode pads (eight shown).

FIG. 13A shows cylindrical electrodes 1304 (eight (8) shown) on the outside of a lead 1300. The outer diameter of lead 1300 may be 0.8 cm or smaller. Each cylindrical electrode 1304 may operate as a recording or stimulating electrode. A stimulating electrode may apply electric pulses to an excitable tissue to achieve therapeutic effect. A recording electrode may record or sense neural activity from surrounding tissue. In some instances, the electrodes may alternate between stimulating and recording electrodes. In the example shown, the miniature lead 1300 is not tethered and not connected to another structure or device for mechanical or electrical interface. One or more electrical flex circuitry may be internal to the miniature lead. The flex circuit may be inside gaps 1306, in between electrodes 1304. Lead 1300 may also include a rounded-tip 1302 for easy placement, as well as a mating feature to mate the lead 1300 with a stylet, such as those described above.

Figure 13B:
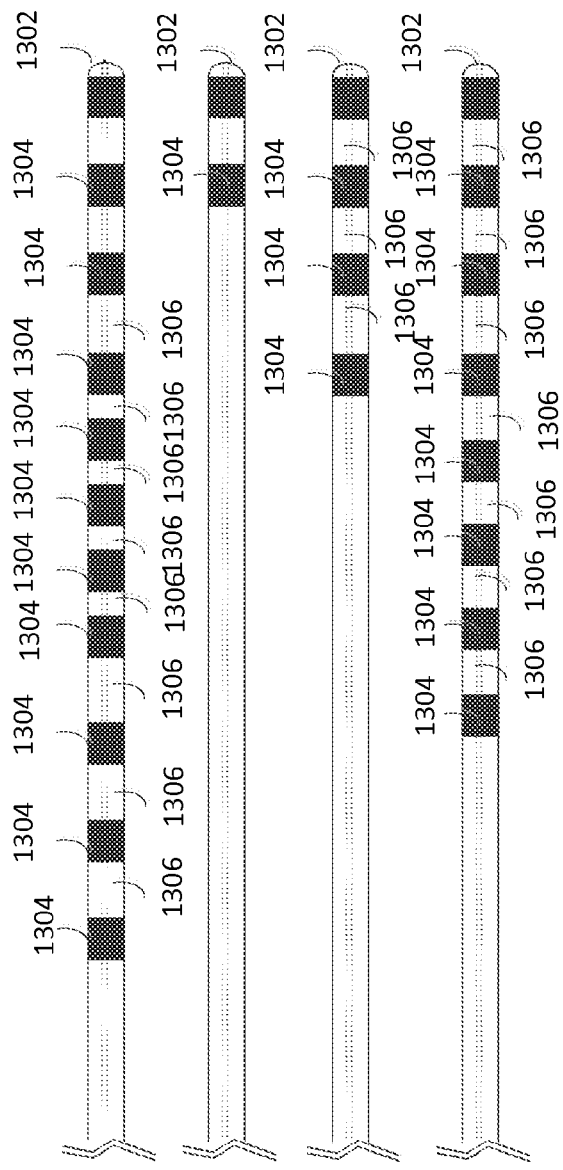
FIG. 13B illustrates various electrode configurations for stimulation and or recording electrodes on the miniature implantable device body, with various inter-electrode spacing options and mixture of recording and stimulation electrode assignments.

FIG. 13B shows four example miniature implantable devices incorporating multiple recording and/or stimulating electrodes 1304. The four example leads shown do not have an inner stylet lumen to mount a stylet or a guide wire, but may include a mating feature such as those described above. The recording and/or stimulating electrode pads 804 may couple to a surrounding tissue for recording and/or stimulating. In a recording mode, neural activities of the surrounding tissue may be sensed and capture in electrical signals that encode such neural activities. In a stimulating mode, electric pulses may be applied to the surrounding tissue for pain relief. In some configurations, the electric circuitry may be spaced in between the recording and/or stimulating electrode pads, for example, in gaps 1306. As illustrated, example miniature implantable devices 1300 may include rounded tip 1302 for easy placement.

Figure 13C:
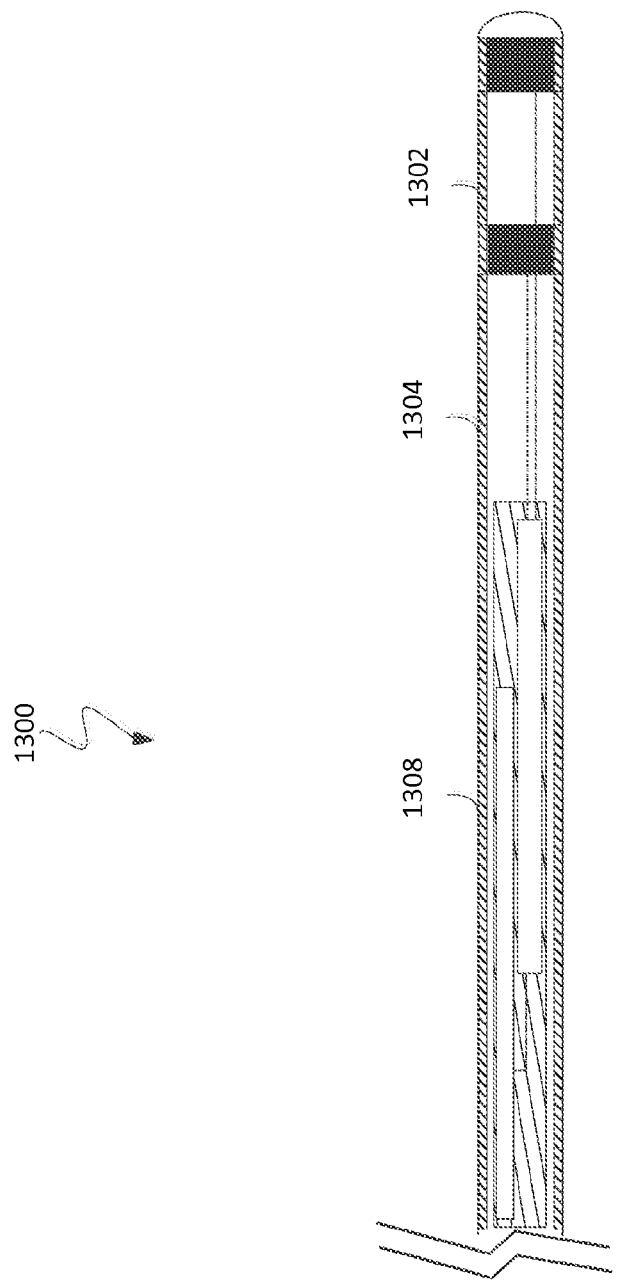
FIG. 13C is a cutout view of a miniature implantable device with stimulation or recording electrodes and the electronic circuitry and wireless power receiver.

FIG. 13C illustrates a miniature implantable device 1300 with stimulating and/or recording electrodes 1304 located at the distal end of the lead, in the direction of the rounded tip 1302. As illustrated, the electronic circuitry 808 is located towards the proximal end of implantable device 1300, rather than spaced between the electrodes 1302.

For the configurations shown in FIGS. 12A to 12C, the electronic circuitry may provide power to drive the stimulating and/or recording electrodes. As described above, the electric pulses may be created by the electronic circuitry based on the input signal received at the antennas on the implantable devices. The electric pulses may be sent to a stimulating electrode to delivery pain-relief to an excitable tissue. As discussed above, a recording electrode may record neural activities of a surrounding tissue. The electronic circuitry also may route the recorded analog signal to the antennas on the implantable device which may in turn transmit the recorded analog signal to an external controller, located outside the patient body. In some implementations, the recorded analog signal may be processed and transmitted in a manner similar to the telemetry signal described above. For example, the transmission of the recorded analog signal, like the telemetry signal discussed herein, may be powered by the electrical power in the input signal.

Figure 14:
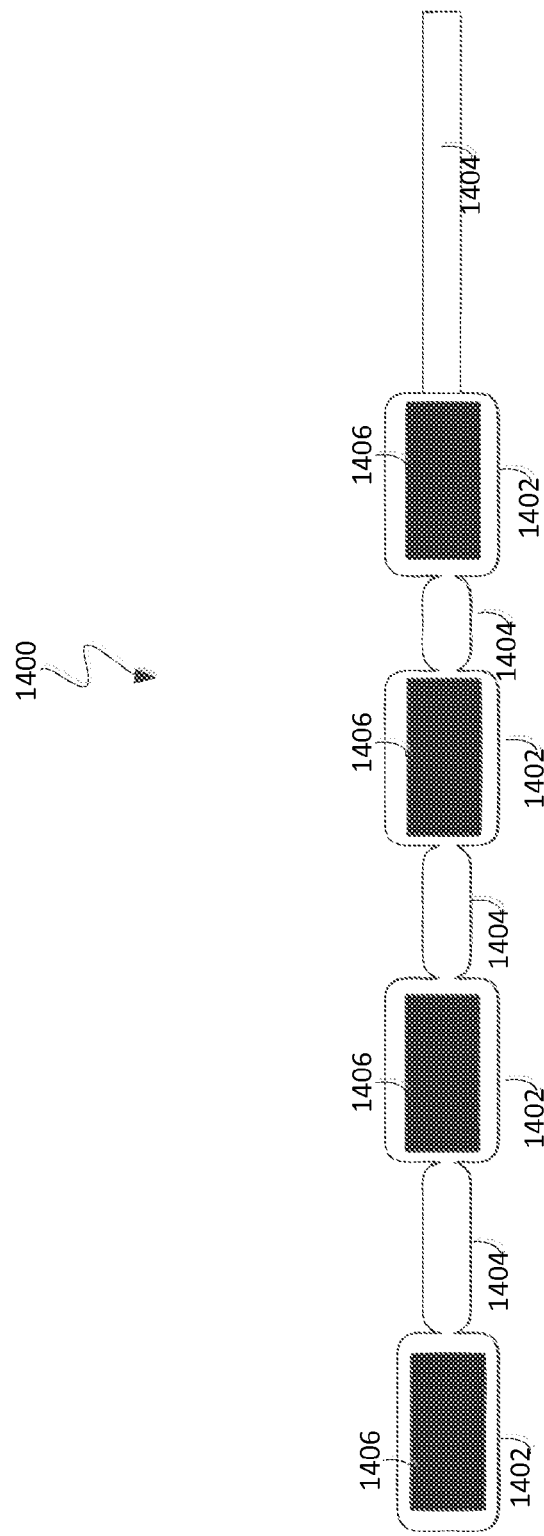
FIG. 14 illustrates a view of a miniature implantable device and a plate electrode configuration for the stimulation or recording pads.

FIG. 14 depicts an example of a lead 1400 with each electrode pad 1402 configured as a rectangular square. As illustrated, each rectangular square electrode pad 1402 may include an electrode 1406. Electronic circuitry may be located on structures 1404. Electrode 906 may have a surface area of at least 0.06 mm2. This implantable device 1400 may have a total width from between about 0.5 mm and 0.8 mm. The height of the implantable device 1400 may be from between about 0.1 mm and about 0.8 mm. The total length of the implantable device 1400 may be from between about 10 mm and about 600 mm. The rectangular electrode pads 1402 may have a length from between about 0.5 mm and about 6.0 mm and a width from between about 0.45 mm and about 0.75 mm. The inter-electrode spacing may be from between about 0.1 mm and about 6.0 mm. This implantable device 1400 may be suitable for stimulating a relatively large area.

Figure 15:
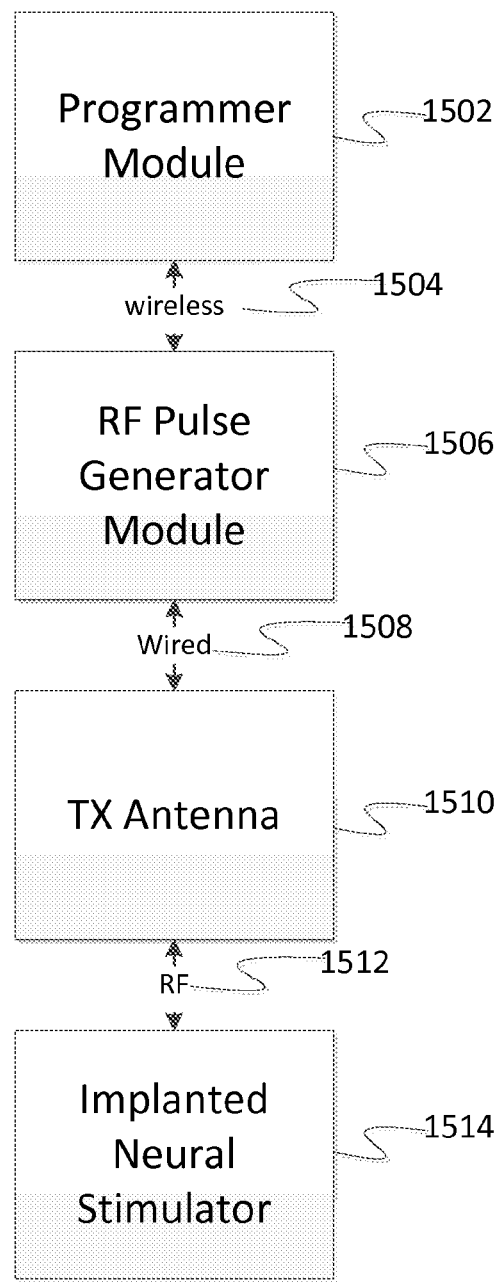
FIG. 15 depicts a high-level diagram of an example of a wireless neural stimulation system.
Figure 16:
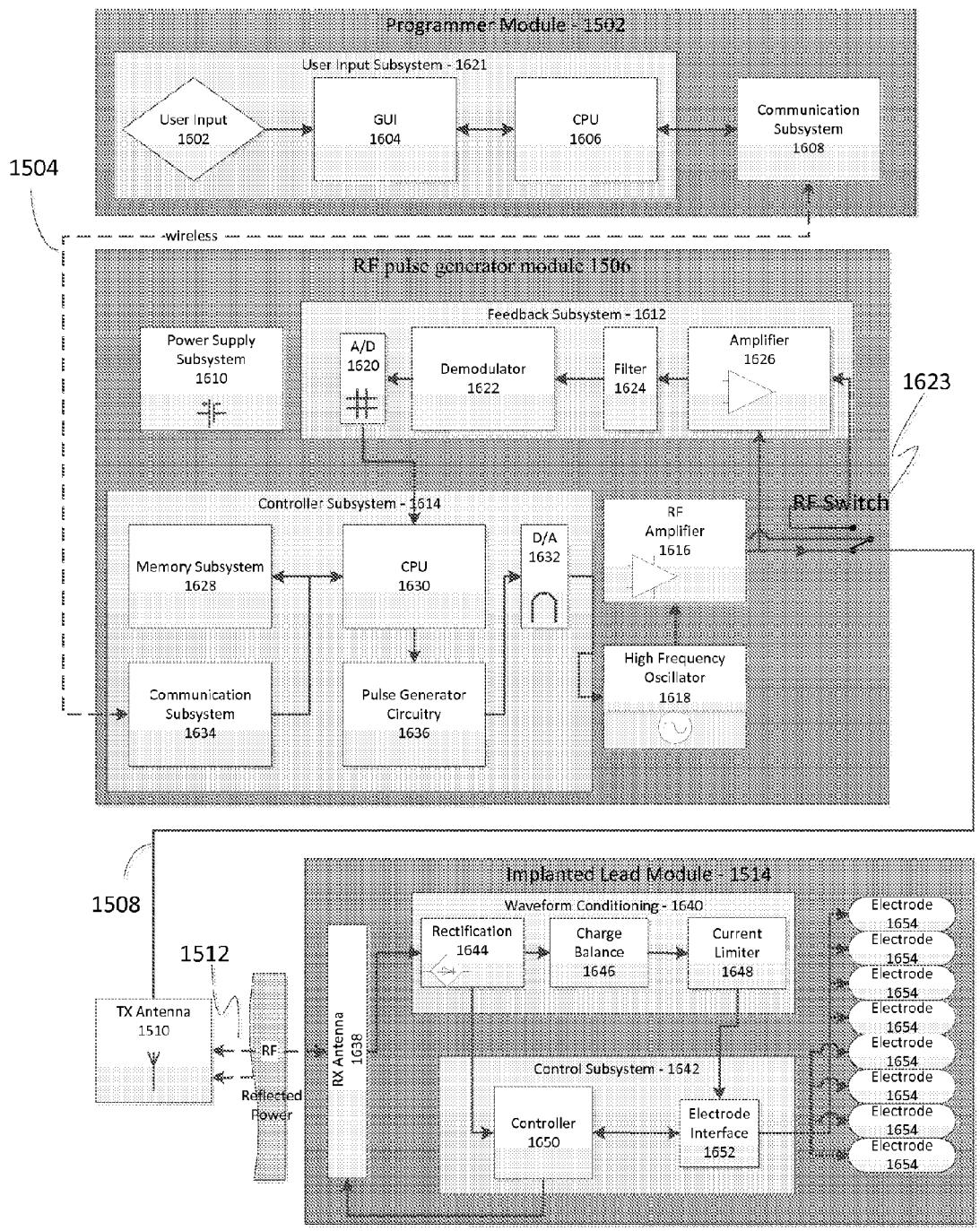
FIG. 16 depicts a detailed diagram of an example of a wireless neural stimulation system.

FIGS. 15 and 16 illustrate an example of a neural stimulation system that may employ the implantable devices described above. These implantable devices may also be referred to as implantable leads.

In particular, FIG. 15 depicts a high-level diagram of an example of a neural stimulation system. The neural stimulation system may include four major components, namely, a programmer module 1502, a RF pulse generator module 1506, a transmit (TX) antenna 1510 (for example, a patch antenna, slot antenna, or a dipole antenna), and an implanted device 1514, which may be a lead such as those described above. The programmer module 1502 may be a computer device, such as a smart phone, running a software application that supports a wireless connection 1514, such as Bluetooth®. The application can enable the user to view the system status and diagnostics, change various parameters, increase/decrease the desired stimulus amplitude of the electrode pulses, and adjust feedback sensitivity of the RF pulse generator module 1506, among other functions.

The RF pulse generator module 1506 may include communication electronics that support the wireless connection 1504, the stimulation circuitry, and the battery to power the generator electronics. In some implementations, the RF pulse generator module 1506 includes the TX antenna embedded into its packaging form factor while, in other implementations, the TX antenna is connected to the RF pulse generator module 1506 through a wired connection 1508 or a wireless connection (not shown). The TX antenna 1510 may be coupled directly to tissue to create an electric field that powers the implanted device 1014. The TX antenna 1510 communicates with the implanted device 1514 through an RF interface. For instance, the TX antenna 1510 radiates an RF transmission signal that is modulated and encoded by the RF pulse generator module 1510. The implanted device 1514 contains one or more antennas, such as dipole antenna(s), to receive and transmit through RF interface 1512. In particular, the coupling mechanism between antenna 1510 and the one or more antennas on the implanted device 1514 is electrical radiative coupling and not inductive coupling. In other words, the coupling is through an electric field rather than a magnetic field.

Through this electrical radiative coupling, the TX antenna 1510 can provide an input signal to the implanted device 1514. This input signal contains energy and may contain information encoding stimulus waveforms to be applied at the electrodes of the implanted device 1514. In some implementations, the power level of this input signal directly determines an applied amplitude (for example, power, current, or voltage) of the one or more electrical pulses created using the electrical energy contained in the input signal. Within the implanted device 1514 are components for demodulating the RF transmission signal, and electrodes to deliver the stimulation to surrounding neuronal tissue.

The RF pulse generator module 1506 can be implanted subcutaneously, or it can be worn external to the body. When external to the body, the RF generator module 1506 can be incorporated into a belt or harness design to allow for electric radiative coupling through the skin and underlying tissue to transfer power and/or control parameters to the implanted device 1514, which can be a passive stimulator. In either event, receiver circuit(s) internal to the device 1514 can capture the energy radiated by the TX antenna 1510 and convert this energy to an electrical waveform. The receiver circuit(s) may further modify the waveform to create an electrical pulse suitable for the stimulation of neural tissue, and this pulse may be delivered to the tissue via electrode pads.

In some implementations, the RF pulse generator module 1506 can remotely control the stimulus parameters (that is, the parameters of the electrical pulses applied to the neural tissue) and monitor feedback from the wireless device 1514 based on RF signals received from the implanted wireless device 1514. A feedback detection algorithm implemented by the RF pulse generator module 1506 can monitor data sent wirelessly from the implanted wireless device 1514, including information about the energy that the implanted wireless device 1514 is receiving from the RF pulse generator and information about the stimulus waveform being delivered to the electrode pads. In order to provide an effective therapy for a given medical condition, the system can be tuned to provide the optimal amount of excitation or inhibition to the nerve fibers by electrical stimulation. A closed loop feedback control method can be used in which the output signals from the implanted wireless device 1514 are monitored and used to determine the appropriate level of neural stimulation current for maintaining effective neuronal activation, or, in some cases, the patient can manually adjust the output signals in an open loop control method.

FIG. 16 depicts a detailed diagram of an example of the neural stimulation system. As depicted, the programming module 1502 may comprise user input system 1602 and communication subsystem 1608. The user input system 1621 may allow various parameter settings to be adjusted (in some cases, in an open loop fashion) by the user in the form of instruction sets. The communication subsystem 1608 may transmit these instruction sets (and other information) via the wireless connection 1504, such as Bluetooth or Wi-Fi, to the RF pulse generator module 1506, as well as receive data from module 1506.

For instance, the programmer module 1502, which can be utilized for multiple users, such as a patient's control unit or clinician's programmer unit, can be used to send stimulation parameters to the RF pulse generator module 1506. The stimulation parameters that can be controlled may include pulse amplitude, pulse frequency, and pulse width in the ranges shown in Table 1. In this context the term pulse refers to the phase of the waveform that directly produces stimulation of the tissue; the parameters of the charge-balancing phase (described below) can similarly be controlled. The patient and/or the clinician can also optionally control overall duration and pattern of treatment.

STIMULATION PARAMETER TABLE 1

| | |
|---|---|
| Pulse Amplitude: | 0 to 20 mA |
| Pulse Frequency: | 0 to 20,000 Hz |
| Pulse Width: | 0 to 2 ms |

The implantable device 1514 or RF pulse generator module 1514 (which may be a lead such as those described above) may be initially programmed to meet the specific parameter settings for each individual patient during the initial implantation procedure. Because medical conditions or the body itself can change over time, the ability to re-adjust the parameter settings may be beneficial to ensure ongoing efficacy of the neural modulation therapy.

The programmer module 1502 may be functionally a smart device and associated application. The smart device hardware may include a CPU 1606 and be used as a vehicle to handle touchscreen input on a graphical user interface (GUI) 1604, for processing and storing data.

The RF pulse generator module 1506 may be connected via wired connection 1508 to an external TX antenna 1510. Alternatively, both the antenna and the RF pulse generator are located subcutaneously (not shown).

The signals sent by RF pulse generator module 1506 to the implanted device 1514 may include both power and parameter-setting attributes in regards to stimulus waveform, amplitude, pulse width, and frequency. The RF pulse generator module 1506 can also function as a wireless receiving unit that receives feedback signals from the implanted device 1514. To that end, the RF pulse generator module 1506 may contain microelectronics or other circuitry to handle the generation of the signals transmitted to the device 1514 as well as handle feedback signals, such as those from the device 1514. For example, the RF pulse generator module 1506 may comprise controller subsystem 1614, high-frequency oscillator 1618, RF amplifier 1616, a RF switch 1623, and a feedback subsystem 1112.

The controller subsystem 1614 may include a CPU 1630 to handle data processing, a memory subsystem 1628 such as a local memory, communication subsystem 1634 to communicate with programmer module 1502 (including receiving stimulation parameters from programmer module), pulse generator circuitry 1636, and digital/analog (D/A) converters 1632.

The controller subsystem 1614 may be used by the patient and/or the clinician to control the stimulation parameter settings (for example, by controlling the parameters of the signal sent from RF pulse generator module 1506 to device 1514). These parameter settings can affect, for example, the power, current level, or shape of the one or more electrical pulses. The programming of the stimulation parameters can be performed using the programming module 1502, as described above, to set the repetition rate, pulse width, amplitude, and waveform that will be transmitted by RF energy to the receive (RX) antenna 1638, typically a dipole antenna (although other types may be used), in the wireless implanted device 1614. The clinician may have the option of locking and/or hiding certain settings within the programmer interface, thus limiting the patient's ability to view or adjust certain parameters because adjustment of certain parameters may require detailed medical knowledge of neurophysiology, neuroanatomy, protocols for neural modulation, and safety limits of electrical stimulation.

The controller subsystem 1614 may store received parameter settings in the local memory subsystem 1628, until the parameter settings are modified by new input data received from the programming module 1502. The CPU 1606 may use the parameters stored in the local memory to control the pulse generator circuitry 1636 to generate a stimulus waveform that is modulated by a high frequency oscillator 1618 in the range from 300 MHz to 8 GHz. The resulting RF signal may then be amplified by RF amplifier 1626 and then sent through an RF switch 1623 to the TX antenna 1510 to reach through depths of tissue to the RX antenna 1638.

In some implementations, the RF signal sent by TX antenna 1510 may simply be a power transmission signal used by the device 1514 to generate electric pulses. In other implementations, a telemetry signal may also be transmitted to the device 1514 to send instructions about the various operations of the device 1514. The telemetry signal may be sent by the modulation of the carrier signal (through the skin if external, or through other body tissues if the pulse generator module 1506 is implanted subcutaneously). The telemetry signal is used to modulate the carrier signal (a high frequency signal) that is coupled onto the implanted antenna(s) 1638 and does not interfere with the input received on the same lead to power the implant. In one embodiment the telemetry signal and powering signal are combined into one signal, where the RF telemetry signal is used to modulate the RF powering signal, and thus the implanted stimulator is powered directly by the received telemetry signal; separate subsystems in the stimulator harness the power contained in the signal and interpret the data content of the signal.

The RF switch 1623 may be a multipurpose device such as a dual directional coupler, which passes the relatively high amplitude, extremely short duration RF pulse to the TX antenna 1510 with minimal insertion loss while simultaneously providing two low-level outputs to feedback subsystem 1612; one output delivers a forward power signal to the feedback subsystem 1612, where the forward power signal is an attenuated version of the RF pulse sent to the TX antenna 1510, and the other output delivers a reverse power signal to a different port of the feedback subsystem 1612, where reverse power is an attenuated version of the reflected RF energy from the TX Antenna 1510.

During the on-cycle time (when an RF signal is being transmitted to the device 1514), the RF switch 1623 is set to send the forward power signal to feedback subsystem. During the off-cycle time (when an RF signal is not being transmitted to the device 1514), the RF switch 1623 can change to a receiving mode in which the reflected RF energy and/or RF signals from the device 1514 are received to be analyzed in the feedback subsystem 1612.

The feedback subsystem 1612 of the RF pulse generator module 1506 may include reception circuitry to receive and extract telemetry or other feedback signals from the device 1514 and/or reflected RF energy from the signal sent by TX antenna 1510. The feedback subsystem may include an amplifier 1626, a filter 1624, a demodulator 1622, and an A/D converter 1620.

The feedback subsystem 1612 receives the forward power signal and converts this high-frequency AC signal to a DC level that can be sampled and sent to the controller subsystem 1614. In this way the characteristics of the generated RF pulse can be compared to a reference signal within the controller subsystem 1614. If a disparity (error) exists in any parameter, the controller subsystem 1614 can adjust the output to the RF pulse generator 1506. The nature of the adjustment can be, for example, proportional to the computed error. The controller subsystem 1614 can incorporate additional inputs and limits on its adjustment scheme such as the signal amplitude of the reverse power and any predetermined maximum or minimum values for various pulse parameters.

The reverse power signal can be used to detect fault conditions in the RF-power delivery system. In an ideal condition, when TX antenna 1510 has perfectly matched impedance to the tissue that it contacts, the electromagnetic waves generated from the RF pulse generator 1506 pass unimpeded from the TX antenna 1510 into the body tissue. However, in real-world applications a large degree of variability may exist in the body types of users, types of clothing worn, and positioning of the antenna 1510 relative to the body surface. Since the impedance of the antenna 1510 depends on the relative permittivity of the underlying tissue and any intervening materials, and also depends on the overall separation distance of the antenna from the skin, in any given application there can be an impedance mismatch at the interface of the TX antenna 1510 with the body surface. When such a mismatch occurs, the electromagnetic waves sent from the RF pulse generator 1006 are partially reflected at this interface, and this reflected energy propagates backward through the antenna feed.

The dual directional coupler RF switch 1623 may prevent the reflected RF energy propagating back into the amplifier 1626, and may attenuate this reflected RF signal and send the attenuated signal as the reverse power signal to the feedback subsystem 1612. The feedback subsystem 1612 can convert this high-frequency AC signal to a DC level that can be sampled and sent to the controller subsystem 1614. The controller subsystem 1614 can then calculate the ratio of the amplitude of the reverse power signal to the amplitude of the forward power signal. The ratio of the amplitude of reverse power signal to the amplitude level of forward power may indicate severity of the impedance mismatch.

In order to sense impedance mismatch conditions, the controller subsystem 1614 can measure the reflected-power ratio in real time, and according to preset thresholds for this measurement, the controller subsystem 1614 can modify the level of RF power generated by the RF pulse generator 1506. For example, for a moderate degree of reflected power the course of action can be for the controller subsystem 1614 to increase the amplitude of RF power sent to the TX antenna 1510, as would be needed to compensate for slightly non-optimum but acceptable TX antenna coupling to the body. For higher ratios of reflected power, the course of action can be to prevent operation of the RF pulse generator 1506 and set a fault code to indicate that the TX antenna 1510 has little or no coupling with the body. This type of reflected-power fault condition can also be generated by a poor or broken connection to the TX antenna. In either case, it may be desirable to stop RF transmission when the reflected-power ratio is above a defined threshold, because internally reflected power can lead to unwanted heating of internal components, and this fault condition means the system cannot deliver sufficient power to the implanted wireless neural stimulator and thus cannot deliver therapy to the user.

The controller 1642 of the device 1514 may transmit informational signals, such as a telemetry signal, through the antenna 1138 to communicate with the RF pulse generator module 1006 during its receive cycle. For example, the telemetry signal from the device 1514 may be coupled to the modulated signal on the dipole antenna(s) 1638, during the on and off state of the transistor circuit to enable or disable a waveform that produces the corresponding RF bursts necessary to transmit to the external (or remotely implanted) pulse generator module 1506. The antenna(s) 1638 may be connected to electrodes 1654 in contact with tissue to provide a return path for the transmitted signal. An A/D (not shown) converter can be used to transfer stored data to a serialized pattern that can be transmitted on the pulse modulated signal from the internal antenna(s) 1638 of the neural stimulator.

A telemetry signal from the implanted wireless device 1514 may include stimulus parameters such as the power or the amplitude of the current that is delivered to the tissue from the electrodes. The feedback signal can be transmitted to the RF pulse generator module 1516 to indicate the strength of the stimulus at the nerve bundle by means of coupling the signal to the implanted RX antenna 1638, which radiates the telemetry signal to the external (or remotely implanted) RF pulse generator module 1506. The feedback signal can include either or both an analog and digital telemetry pulse modulated carrier signal. Data such as stimulation pulse parameters and measured characteristics of stimulator performance can be stored in an internal memory device within the implanted device 1514, and sent on the telemetry signal. The frequency of the carrier signal may be in the range of at 300 MHz to 8 GHz.

In the feedback subsystem 1612, the telemetry signal can be down modulated using demodulator 1622 and digitized by being processed through an analog to digital (A/D) converter 1620. The digital telemetry signal may then be routed to a CPU 1630 with embedded code, with the option to reprogram, to translate the signal into a corresponding current measurement in the tissue based on the amplitude of the received signal. The CPU 1630 of the controller subsystem 1614 can compare the reported stimulus parameters to those held in local memory 1628 to verify the stimulator(s) 1514 delivered the specified stimuli to tissue. For example, if the stimulator reports a lower current than was specified, the power level from the RF pulse generator module 1506 can be increased so that the implanted neural stimulator 1514 will have more available power for stimulation. The implanted neural stimulator 1514 can generate telemetry data in real time, for example, at a rate of 8 kbits per second. All feedback data received from the implanted lead module 1514 can be logged against time and sampled to be stored for retrieval to a remote monitoring system accessible by the health care professional for trending and statistical correlations.

The sequence of remotely programmable RF signals received by the internal antenna(s) 1638 may be conditioned into waveforms that are controlled within the implantable device 1514 by the control subsystem 1642 and routed to the appropriate electrodes 1654 that are placed in proximity to the tissue to be stimulated. For instance, the RF signal transmitted from the RF pulse generator module 1506 may be received by RX antenna 1638 and processed by circuitry, such as waveform conditioning circuitry 1140, within the implanted wireless device 1514 to be converted into electrical pulses applied to the electrodes 1654 through electrode interface 1652. In some implementations, the implanted device 1514 contains between two to sixteen electrodes 1654.

The waveform conditioning circuitry 1640 may include a rectifier 1644, which rectifies the signal received by the RX antenna 1638. The rectified signal may be fed to the controller 1642 for receiving encoded instructions from the RF pulse generator module 1506. The rectifier signal may also be fed to a charge balance component 1646 that is configured to create one or more electrical pulses based such that the one or more electrical pulses result in a substantially zero net charge at the one or more electrodes (that is, the pulses are charge balanced). The charge-balanced pulses are passed through the current limiter 1648 to the electrode interface 1652, which applies the pulses to the electrodes 1654 as appropriate.

The current limiter 1648 insures the current level of the pulses applied to the electrodes 1654 is not above a threshold current level. In some implementations, an amplitude (for example, current level, voltage level, or power level) of the received RF pulse directly determines the amplitude of the stimulus. In this case, it may be particularly beneficial to include current limiter 1648 to prevent excessive current or charge being delivered through the electrodes, although current limiter 1648 may be used in other implementations where this is not the case. Generally, for a given electrode having several square millimeters surface area, it is the charge per phase that should be limited for safety (where the charge delivered by a stimulus phase is the integral of the current). But, in some cases, the limit can instead be placed on the current, where the maximum current multiplied by the maximum possible pulse duration is less than or equal to the maximum safe charge. More generally, the limiter 1648 may act as a charge limiter that limits a characteristic (for example, current or duration) of the electrical pulses so that the charge per phase remains below a threshold level (typically, a safe-charge limit).

In the event the implanted wireless device 1614 receives a "strong" pulse of RF power sufficient to generate a stimulus that would exceed the predetermined safe-charge limit, the current limiter 1648 can automatically limit or "clip" the stimulus phase to maintain the total charge of the phase within the safety limit. The current limiter 1648 may be a passive current limiting component that cuts the signal to the electrodes 1654 once the safe current limit (the threshold current level) is reached. Alternatively, or additionally, the current limiter 1648 may communicate with the electrode interface 1652 to turn off all electrodes 1654 to prevent tissue damaging current levels.

A clipping event may trigger a current limiter feedback control mode. The action of clipping may cause the controller to send a threshold power data signal to the pulse generator 1506. The feedback subsystem 1612 detects the threshold power signal and demodulates the signal into data that is communicated to the controller subsystem 1614. The controller subsystem 1614 algorithms may act on this current-limiting condition by specifically reducing the RF power generated by the RF pulse generator, or cutting the power completely. In this way, the pulse generator 1506 can reduce the RF power delivered to the body if the implanted wireless neural stimulator 1514 reports it is receiving excess RF power.

The controller 1650 of the device 1605 may communicate with the electrode interface 1652 to control various aspects of the electrode setup and pulses applied to the electrodes 1654. The electrode interface 1652 may act as a multiplex and control the polarity and switching of each of the electrodes 1654. For instance, in some implementations, the wireless stimulator 1506 has multiple electrodes 1154 in contact with tissue, and for a given stimulus the RF pulse generator module 1506 can arbitrarily assign one or more electrodes to 1) act as a stimulating electrode, 2) act as a return electrode, or 3) be inactive by communication of assignment sent wirelessly with the parameter instructions, which the controller 1650 uses to set electrode interface 1652 as appropriate. It may be physiologically advantageous to assign, for example, one or two electrodes as stimulating electrodes and to assign all remaining electrodes as return electrodes.

Also, in some implementations, for a given stimulus pulse, the controller 1650 may control the electrode interface 1652 to divide the current arbitrarily (or according to instructions from pulse generator module 1506) among the designated stimulating electrodes. This control over electrode assignment and current control can be advantageous because in practice the electrodes 1654 may be spatially distributed along various neural structures, and through strategic selection of the stimulating electrode location and the proportion of current specified for each location, the aggregate current distribution in tissue can be modified to selectively activate specific neural targets. This strategy of current steering can improve the therapeutic effect for the patient.

In another implementation, the time course of stimuli may be arbitrarily manipulated. A given stimulus waveform may be initiated at a time T_start and terminated at a time T_final, and this time course may be synchronized across all stimulating and return electrodes; further, the frequency of repetition of this stimulus cycle may be synchronous for all the electrodes. However, controller 1650, on its own or in response to instructions from pulse generator 1506, can control electrode interface 1652 to designate one or more subsets of electrodes to deliver stimulus waveforms with non-synchronous start and stop times, and the frequency of repetition of each stimulus cycle can be arbitrarily and independently specified.

For example, a stimulator having eight electrodes may be configured to have a subset of five electrodes, called set A, and a subset of three electrodes, called set B. Set A might be configured to use two of its electrodes as stimulating electrodes, with the remainder being return electrodes. Set B might be configured to have just one stimulating electrode. The controller 1650 could then specify that set A deliver a stimulus phase with 3 mA current for a duration of 200 us followed by a 400 us charge-balancing phase. This stimulus cycle could be specified to repeat at a rate of 60 cycles per second. Then, for set B, the controller 1650 could specify a stimulus phase with 1 mA current for duration of 500 us followed by a 800 us charge-balancing phase. The repetition rate for the set-B stimulus cycle can be set independently of set A, say for example it could be specified at 25 cycles per second. Or, if the controller 1650 was configured to match the repetition rate for set B to that of set A, for such a case the controller 1650 can specify the relative start times of the stimulus cycles to be coincident in time or to be arbitrarily offset from one another by some delay interval.

In some implementations, the controller 1650 can arbitrarily shape the stimulus waveform amplitude, and may do so in response to instructions from pulse generator 1006. The stimulus phase may be delivered by a constant-current source or a constant-voltage source, and this type of control may generate characteristic waveforms that are static, e.g. a constant-current source generates a characteristic rectangular pulse in which the current waveform has a very steep rise, a constant amplitude for the duration of the stimulus, and then a very steep return to baseline. Alternatively, or additionally, the controller 1650 can increase or decrease the level of current at any time during the stimulus phase and/or during the charge-balancing phase. Thus, in some implementations, the controller 1650 can deliver arbitrarily shaped stimulus waveforms such as a triangular pulse, sinusoidal pulse, or Gaussian pulse for example. Similarly, the charge-balancing phase can be arbitrarily amplitude-shaped, and similarly a leading anodic pulse (prior to the stimulus phase) may also be amplitude-shaped.

As described above, the device 1514 may include a charge-balancing component 1646. Generally, for constant current stimulation pulses, pulses should be charge balanced by having the amount of cathodic current should equal the amount of anodic current, which is typically called biphasic stimulation. Charge density is the amount of current times the duration it is applied, and is typically expressed in the units of $uC/cm^2$. In order to avoid the irreversible electrochemical reactions such as pH change, electrode dissolution as well as tissue destruction, no net charge should appear at the electrode-electrolyte interface, and it is generally acceptable to have a charge density less than 30 $uC/cm^2$. Biphasic stimulating current pulses ensure that no net charge appears at the electrode after each stimulation cycle and the electrochemical processes are balanced to prevent net dc currents. The device 1514 may be designed to ensure that the resulting stimulus waveform has a net zero charge. Charge balanced stimuli are thought to have minimal damaging effects on tissue by reducing or eliminating electrochemical reaction products created at the electrode-tissue interface.

A stimulus pulse may have a negative-voltage or current, called the cathodic phase of the waveform. Stimulating electrodes may have both cathodic and anodic phases at different times during the stimulus cycle. An electrode that delivers a negative current with sufficient amplitude to stimulate adjacent neural tissue is called a "stimulating electrode." During the stimulus phase the stimulating electrode acts as a current sink. One or more additional electrodes act as a current source and these electrodes are called "return electrodes." Return electrodes are placed elsewhere in the tissue at some distance from the stimulating electrodes. When a typical negative stimulus phase is delivered to tissue at the stimulating electrode, the return electrode has a positive stimulus phase. During the subsequent charge-balancing phase, the polarities of each electrode are reversed.

In some implementations, the charge balance component 1646 uses a blocking capacitor(s) placed electrically in series with the stimulating electrodes and body tissue, between the point of stimulus generation within the stimulator circuitry and the point of stimulus delivery to tissue. In this manner, a resistor-capacitor (RC) network may be formed. In a multi-electrode stimulator, one charge-balance capacitor(s) may be used for each electrode or a centralized capacitor(s) may be used within the stimulator circuitry prior to the point of electrode selection. The RC network can block direct current (DC), however it can also prevent low-frequency alternating current (AC) from passing to the tissue. The frequency below which the series RC network essentially blocks signals is commonly referred to as the cutoff frequency, and in one embodiment the design of the stimulator system may ensure the cutoff frequency is not above the fundamental frequency of the stimulus waveform. In this embodiment of the present invention, the wireless stimulator may have a charge-balance capacitor with a value chosen according to the measured series resistance of the electrodes and the tissue environment in which the stimulator is implanted. By selecting a specific capacitance value the cutoff frequency of the RC network in this embodiment is at or below the fundamental frequency of the stimulus pulse.

In other implementations, the cutoff frequency may be chosen to be at or above the fundamental frequency of the stimulus, and in this scenario the stimulus waveform created prior to the charge-balance capacitor, called the drive waveform, may be designed to be non-stationary, where the envelope of the drive waveform is varied during the duration of the drive pulse. For example, in one embodiment, the initial amplitude of the drive waveform is set at an initial amplitude $V_i$, and the amplitude is increased during the duration of the pulse until it reaches a final value $k*V_i$. By changing the amplitude of the drive waveform over time, the shape of the stimulus waveform passed through the charge-balance capacitor is also modified. The shape of the stimulus waveform may be modified in this fashion to create a physiologically advantageous stimulus.

In some implementations, the wireless device 1514 may create a drive-waveform envelope that follows the envelope of the RF pulse received by the receiving dipole antenna(s) 1638. In this case, the RF pulse generator module 1506 can directly control the envelope of the drive waveform within the wireless device 1514, and thus no energy storage may be required inside the stimulator itself. In this implementation, the stimulator circuitry may modify the envelope of the drive waveform or may pass it directly to the charge-balance capacitor and/or electrode-selection stage.

In some implementations, the implanted device 1514 may deliver a single-phase drive waveform to the charge balance capacitor or it may deliver multiphase drive waveforms. In the case of a single-phase drive waveform, for example, a negative-going rectangular pulse, this pulse comprises the physiological stimulus phase, and the charge-balance capacitor is polarized (charged) during this phase. After the drive pulse is completed, the charge balancing function is performed solely by the passive discharge of the charge-balance capacitor, where is dissipates its charge through the tissue in an opposite polarity relative to the preceding stimulus. In one implementation, a resistor within the stimulator facilitates the discharge of the charge-balance capacitor. In some implementations, using a passive discharge phase, the capacitor may allow virtually complete discharge prior to the onset of the subsequent stimulus pulse.

In the case of multiphase drive waveforms the wireless stimulator may perform internal switching to pass negative-going or positive-going pulses (phases) to the charge-balance capacitor. These pulses may be delivered in any sequence and with varying amplitudes and waveform shapes to achieve a desired physiological effect. For example, the stimulus phase may be followed by an actively driven charge-balancing phase, and/or the stimulus phase may be preceded by an opposite phase. Preceding the stimulus with an opposite-polarity phase, for example, can have the advantage of reducing the amplitude of the stimulus phase required to excite tissue.

In some implementations, the amplitude and timing of stimulus and charge-balancing phases is controlled by the amplitude and timing of RF pulses from the RF pulse generator module 1006, and in others this control may be administered internally by circuitry onboard the wireless device 1514, such as controller 1650. In the case of onboard control, the amplitude and timing may be specified or modified by data commands delivered from the pulse generator module 1506.

A number of implementations have been described. Nevertheless, it will be understood that various modifications may be made. Accordingly, other implementations are within the scope of the following claims.

What is claimed is:

1. A method for treating craniofacial pain in a patient's body, the method comprising:
   placing a wirelessly powered passive device through an opening into a target site in a head or neck region of the patient's body, the wirelessly powered passive device comprising one or more dipole antenna configured to receive an input signal non-inductively from an external antenna;
   positioning the wirelessly powered passive device such that electrodes of the wireless powered passive device are positioned adjacent to or near a nerve at the target site; and
   delivering a neural modulation to the nerve by causing one or more stimulation pulses to be applied through the electrodes on the wirelessly powered passive device; and
   withdrawing an introducer device from the patient's body after the one or more stimulation pulses have been applied through the electrodes to deliver the neural modulation,
   wherein the one or more stimulation pulses are created solely from electrical energy contained in the input signal, and wherein applying the one or more stimulation pulses results in substantially zero net charge.

2. The method of claim 1, wherein placing the wirelessly powered passive device comprises:
   advancing the wirelessly powered passive device through an inner lumen of an introducer with a size of 14 gauge or smaller.

3. The method of claim 1, wherein placing the wirelessly powered passive device comprises:
   placing the wirelessly powered passive device through a surgical incision made on the patient's body.

4. The method of claim 1, wherein placing the wirelessly powered passive device comprises:
   placing the wirelessly powered passive device percutaneously into the patient's body.

5. The method of claim 1, wherein placing the wirelessly powered passive device comprises:
   placing the wirelessly powered passive device subcutaneously into the patient's body.

6. The method of claim 1, wherein positioning the wirelessly powered passive device comprises:
   advancing a wirelessly powered passive device paddle to reach the nerve at the target site.

7. The method of claim 1, wherein positioning the wirelessly powered passive device comprises:
   advancing a wirelessly powered passive device that is no larger than 0.8 mm in diameter to reach the nerve at the target site.

8. The method of claim 1, wherein causing neural modulation comprises:
   causing neural modulation to a occipital nerve or branches thereof.

9. The method of claim 1, wherein causing neural modulation comprises:
   causing neural modulation to a trochlear nerve or branches thereof.

10. The method of claim 1, wherein causing neural modulation comprises:
    causing neural modulation to a nerve in the patient's body, the nerve including one of: an occipital nerve, a vagus nerve, a trigeminal nerve, a glossopharyngeal nerve, a mandibular nerve, an alveolar nerve, a lingual nerve, a maxillary nerve, a ciliary nerve, a sphenopalatine ganglion, or a supratrochlear nerve.

11. The method of claim 1, further comprising:
    using X-Ray fluoroscopy to guide positioning of the wirelessly powered passive device adjacent to or near the nerve at the target site.

12. The method of claim 1, further comprising:
    using ultrasound sonography to guide positioning of the wirelessly powered passive device adjacent to or near the nerve at the target site.

13. The method of claim 1, wherein causing the neural modulation comprises:
    causing the input signal to be transmitted from the external antenna outside the patient's body, the input signal including electrical power and excitation pulses to drive the electrodes of the wirelessly powered passive device;
    causing the input signal to be received non-inductively by one or more antennas on the wirelessly powered passive device;
    causing the electrical power and excitation pulses to be extracted from the input signal; and
    based on the electrical power, causing the excitation pulses to be delivered to the one or more electrodes on the wirelessly powered passive device.

14. The method of claim 1, wherein placing a wirelessly powered passive device further comprises placing a wirelessly powered passive device that includes (i) electronic circuitry coupled to each of the one or more dipole antennas and configured to extract electric power and information encoding the one or more stimulation pulses from the input signal as received by the one or more dipole antennas.

\* \* \* \* \*

UNITED STATES PATENT AND TRADEMARK OFFICE
CERTIFICATE OF CORRECTION

PATENT NO. : 10,463,858 B2
APPLICATION NO. : 14/775455
DATED : November 5, 2019
INVENTOR(S) : Laura Tyler Perryman and Chad Andresen Page 1 of 1

It is certified that error appears in the above-identified patent and that said Letters Patent is hereby corrected as shown below:

On the Title Page

Column 1, item (71), delete "Miamia" and insert --Miami--, therefor.

Signed and Sealed this
Sixteenth Day of June, 2020

Andrei Iancu
*Director of the United States Patent and Trademark Office*